United States Patent [19]
Pepper et al.

[11] Patent Number: 5,585,921
[45] Date of Patent: Dec. 17, 1996

[54] LASER-ULTRASONIC NON-DESTRUCTIVE, NON-CONTACTING INSPECTION SYSTEM

[75] Inventors: David M. Pepper; Thomas R. O'Meara, both of Malibu; Phillip V. Mitchell, Simi Valley; Gilmore J. Dunning, Newbury Park; Marvin B. Klein, Pacific Palisades, all of Calif.

[73] Assignee: Hughes Aircraft Company, Los Angeles, Calif.

[21] Appl. No.: 404,660

[22] Filed: Mar. 15, 1995

[51] Int. Cl.$^6$ ....................................................... G01B 9/02
[52] U.S. Cl. ........................................... 356/357; 356/432
[58] Field of Search ..................................... 356/349, 351, 356/352, 357, 358, 432 T; 73/655, 657

[56] References Cited

U.S. PATENT DOCUMENTS

| | | | |
|---|---|---|---|
| 4,541,280 | 9/1985 | Cielo et al. | 73/662 |
| 4,581,939 | 4/1986 | Takahashi | 73/655 |
| 4,911,537 | 3/1990 | Ewbank . | |
| 4,991,177 | 2/1991 | Chang et al. . | |
| 5,121,339 | 6/1992 | Jenuwine et al. . | |

OTHER PUBLICATIONS

Matsuda et al., "Optical Detection of Transient Lamb Waves on Rough Surfaces by a Phase–Conjugate Method", *Japanese Journal of Applied Physics*, vol. 31, pp. 987–989 (1992).
Ing et al., "Broadband Optical Detection of Ultrasound by Two–Wave Mixing in a Photorefractive Crystal", *Applied Physics Letters*, vol. 59, pp. 3233–3235 (1991).
Paul et al., "Interferometric Detection of Ultrasound at Rough Surfaces Using Optical Phase Conjugation", *Applied Physics Letters*, vol. 50, pp. 1569–1571 (1987).
Blouin, "Detection of Ultrasonic Motion of a Scattering Surface by Two–Wave Mixing in a Photorefractive GaAs Crystal", *Applied Physics Letters*, vol. 65, pp. 3932–3934 (1994).

Monchalin, "Optical Detection of Ultrasound at a Distance Using a Confocal Fabry–Perot Interferometer", *Applied Physics Letters*, vol. 47, pp. 14–16 (1985).
Celestino J. Gaeta et al., "Characteristics of Innovative Adaptive–Optics Servos That Use Membrane–Based Spatial Light Modulators", *J. Opt. Soc. Am. A.*, vol. 11, No. 2, pp. 880–894 (1994).
Delaye, et al., "Heterodyne Detection of Ultrasound from Rough Surfaces Using a Double Phase Conjugate Mirror", *Applied Physics Letters*, vol. 67, pp. 3251–3253 (1995).
Nakano et al., "Optical Detection of Ultrasound on Rough Surfaces by a Phase–Conjugate Method", *Ultrasonics*, vol. 33, No. 4, pp. 261–264 (1995).
C. B. Scruby and L. E. Drain, *Laser Ultrasonics, Techniques and Applications*, Adam Hilger, New York (1990), pp. 325–350.

*Primary Examiner*—Samuel A. Turner
*Attorney, Agent, or Firm*—V. D. Duraiswamy; W. K. Denson-Low

[57] ABSTRACT

A laser-ultrasonic inspection system is provided for on-line and off-line inspection of a workpiece. The system utilizes an optical acoustic wave generation and detection system with relatively high spatial resolution and which appreciably reduces the effects of parasitic acoustic coupling. An array of acoustic waves are generated in the workpiece by a short pulse optical transmitter bee with a beam geometry that is tailored to focus the acoustic waves at an inspection site in the workpiece. The acoustic waves that probe the inspection site are then detected by reflecting an optical read-out beam from a surface of the workpiece and optically interfering it with an optical reference beam. The geometry of the optical read-out beam is chosen such that the read-out beam only detects the acoustic waves that arrive from the inspection site (acoustic waves that arrive from other parasitic acoustic sources are out of phase with respect to each other and cancel out). A wavefront compensation system improves acoustic clutter rejection and also improves the signal-to-noise by compensating for phase and amplitude aberrations induced on the optical read-out beam by the optically rough surface of the workpiece.

69 Claims, 12 Drawing Sheets

LASER-ULTRASONIC NON-DESTRUCTIVE, NON-CONTACTING INSPECTION SYSTEM

BACKGROUND OF THE INVENTION

1. Field of the Invention

This invention relates to weld inspection systems and more specifically to an efficient, non-contacting, laser-ultrasonic weld inspection system for on-line and off-line use.

2. Description Of the Related Art

Automated welding systems are commonly used in many industrial applications. During the welding process, various factors can introduce structural flaws and defects in the weld, causing a reduction in the fusion width, and hence the strength and reliability of the welded part.

These defects are often hidden and impossible to observe visually. For example, the fusion width of the weld band may be of an incorrect size, the defect could be a small crack in the weld, or the weld itself may be located between layers of opaque material. In addition, typical automated weld systems operate at high throughput speeds. Therefore, a weld defect caused by a malfunction in the welding system could be reproduced many times before the problem is discovered.

Consequently, there is a need for reliable and accurate weld inspections systems that are fast enough to keep up with automated welding systems. Ideally, the weld inspection system should be capable of on-line operation to diagnose faulty welds early in the welding process. In addition, the on-line system should be capable of use as a transducer in a closed-loop welder control system, so that each weld is optimally formed and is certified to a given specification. The system should also have high spatial resolution in order to detect very small defects in the weld that would otherwise go undetected.

There are several off-line and on-line techniques available for weld inspection. One off-line technique involves taking sample parts from the assembly process on a periodic basis and analyzing the welds. Frequently, the analysis involves breaking or sawing through the weld itself to determine its strength and/or size. However, this technique destroys potentially useful parts in the process. In addition, since only the samples are analyzed, many untested welds or weld areas (which may exist immediately adjacent to the sectioned region) are allowed to pass through untested, resulting in a statistically unreliable evaluation procedure.

Some of the prior on-line techniques, such as that disclosed in U.S. Pat. No. 5,121,339, entitled "LASER WELD FAULT DETECTION SYSTEM", issued Jun. 9, 1992 to D. Jenuwine, et. al., analyze the weld during the welding process by sampling and analyzing high frequency emissions that emanate from the weld itself. The high frequency emissions are sampled either directly by using ultrasonic sensors that are placed in physical contact with the part being welded, or indirectly by non-contacting sensors that sense and analyze the airborne emissions from the weld.

The contacting acoustic emission detection systems are expensive, unreliable, and difficult to set up and calibrate. The non-contacting emission detection systems are difficult to calibrate, especially if weld conditions are not identical from part to part. In addition, the non-contacting systems are very sensitive to ambient noise, which can reduce the accuracy of the weld analysis.

Neither of these emission detection systems are very effective in giving detailed information about the weld. They are more useful for qualitative pass/fail determinations rather than quantitative, high resolution information about the weld.

Furthermore, existing contacting and close proximity systems can not be readily implemented in the adverse environments that are typically found in the case of in-factory operation. These environments may include high temperature, plasma, vacuum, or radiation environments. In addition, existing systems are not robust, because they must be "matched" to the surface contours of a given workpiece.

Laser-ultrasonic techniques have been used in both on-line and off-line systems. For some examples of laser-ultrasonic flaw detection techniques, see C. B. Scruby and L. E. Drain, *Laser Ultrasonics, Techniques and Applications*, Adam Hilger, New York (1990), pages 325–350. The technique typically used by prior laser-ultrasonic systems is illustrated in FIGS. 1a and 1b.

A pulsed transmitter laser beam 20 is focused to a single spot 22 on the outer surface 24 of a workpiece 26, typically made of metal, with an internal crack or flaw 32. The transmitter beam 20 generates acoustic waves 28 in the first workpiece 26 which propagate over a broad angular range, so that a portion of the waves 28 illuminate the flaw 32. The acoustic waves 28 are reflected by the flaw 32 to a second workpiece surface 30, and cause the surface 30 to vibrate. A read-out laser beam 36 is focused to a spot 38 on the second workpiece surface 30. The vibrations induced by the reflected acoustic waves 31 phase modulate the read-out beam 36, which is reflected by the second surface 30. The reflected, modulated read-out beam is then optically interfered with a reference beam (not shown) or is directed to a frequency discriminator, such as a Fabry Perot cavity, and the resulting interference pattern is analyzed by receiver electronics to extract information about the existence and size of the flaw 32.

Since the amount of acoustic energy that is reflected to the second workpiece surface 30 increases as the size of the flaw 32 increases, this technique can be used to determine both the existence and the size of the flaw 32, as illustrated by the example of a signal vs. time plot of FIG. 1b.

One of the problems with this technique is illustrated in FIGS. 1c and 1d. In many cases, parasitic acoustic coupling paths are present in the system. These parasitic paths could be formed by reflection of acoustic waves from an edge 39 of the workpiece 26, or from other flaws. The parasitic acoustic waves 42 that are reflected from the edge 39 can interfere with or even dominate the acoustic signal detected by the read-out beam 36. This could greatly disturb and, in some instances, completely void the measurement process as illustrated in the signal vs. time plot of FIG. 1d.

Another problem with prior laser-ultrasonic systems that utilize interferometric laser receivers is that the efficiency of the coherent detection required for interferometric measurements is greatly reduced when the read-out beam is reflected from the rough surface of the welded workpiece. Since the reflected read-out beam is being coherently combined with a reference beam, the read-out beam must have temporal and spatial coherence relative to the reference beam. The reflection from the rough surface produces a "speckle" field distribution on the optical detector that is used to detect the interference pattern. The spatial coherence of the reflected read-out beam is only maintained over a single "speckle" width. If the phase aberrations on the reflected read-out beam are not corrected (or compensated), only a small part or, equivalently, a single spatial mode of the reflected read-out beam will be able to coherently combine with the reference beam (only the area of the reflected read-out beam over which spatial coherence is maintained). The resulting detector signal is thousands of times weaker than it would have been if the surface of the welded workpiece had been a perfect mirror surface.

There are several schemes which employ some form of robust laser ultrasonic receiver to sense minute vibrations at high bandwidths in the presence of rough-cut workpiece surfaces:

(1) Phase-Conjugate Compensation Scheme

Systems that utilize phase-conjugate compensation schemes, such as those described in Paul et al., "Interferometric detection of ultrasound at rough surfaces using optical phase conjugation", Applied Physics Letters, Vol. 50, pages 1569–1571 (1987), and Matsuda et al., "Optical Detection of Transient Lamb Waves on Rough Surfaces by a Phase-Conjugate Method", Japanese Journal of Applied Physics, Vol. 31, pages 987–989 (1992), utilize a double-pass optical architecture in which a laser probe beam illuminates the workpiece surface under inspection. The probe beam is modified temporally (by the desired ultrasound) and spatially (by the rough workpiece surface). The probe beam portion that is scattered and/or reflected by the workpiece surface is directed onto a phase-conjugate mirror. The conjugate wave (wavefront-reversed replica of the scattered and/or reflected probe beam) then retraces its path back to the workpiece surface and, after reflection from the surface, has its spatial wavefront restored back to its initial (planar) wavefront. However, the conjugate wave (return beam) is now "doubly" encoded with the desired ultrasound information as a result of the two reflections from the workpiece surface. The fact that the return beam is now planar enables one to more efficiently detect the ultrasound via coherent detection techniques.

There are drawbacks to this approach. First, unless all the scattered light is collected, the return beam's wavefront will not be perfectly restored to its original planar shape. Second, the beam must be reflected twice off the rough workpiece surface. If the workpiece surface has low reflectivity, the detected optical power will be greatly reduced. If there are local reflectivity "drop-outs" on the workpiece surface (due to scratches, digs, rust spots, blemishes, etc.), the spatial amplitude drop-outs will be impressed onto the double-reflected return beam, resulting in a reduction in the sensitivity of the system.

(2) Two-Wave Mixing Schemes

In systems that utilize a two-wave mixing scheme, such as the ones described in Ing et al., "Broadband optical detection of ultrasound by two-wave mixing in a photorefractive crystal", Applied Physics Letters, Vol. 59, pages 3233–3235 (1991), and Blouin et al., "Detection of ultrasonic motion of a scattering surface by two-wave mixing in a photorefractive GaAs crystal", Applied Physics Letters, Vol. 65, pages 932–934 (1994), only a single pass off the workpiece surface is required. The reflected signal beam is combined in a photorefractive crystal with a planar "pump" beam. Energy from the planar pump beam is diverted in the direction of the aberrated signal beam. The pump beam forms the local oscillator, so that coherent detection (either homodyne or heterodyne) can be performed. These schemes suffer from several problems. First, the pump beam must be coherent with respect to the signal beam over a period of time equal to the response time of the photorefractive crystal. Coherence is required to form the photorefractive gratings required for energy exchange between the beams.

Second, if the reflected signal beam going into the photorefractive crystal is highly speckled, the resultant output beam will likewise be speckled, causing amplitude fluctuations that reduce the signal-to-noise ratio by a factor of approximately 2. In addition, the intensity fluctuations that also arise from speckle may cause local depletion effects that adversely affect the wavefront matching between the signal and diverted pump waves. This will create a spatial mismatch between the signal and pump waves, which will result in reduced coherent detection sensitivity.

(3) Fabry Perot Cavity Scheme

Systems that utilize this scheme, such as the one described in Monchalin, "Optical detection of ultrasound at a distance using a confocal Fabry-Perot interferometer" Applied Physics Letters, Vol. 47, pages 14–16 (1985), utilize a Fabry Perot interferometer, which is basically a time-delayed, self-referencing interferometer (also called a "discriminator"), whose output is proportional to the velocity of the surface under inspection. In contrast, the two schemes described above measure the displacement of the workpiece surface. The Fabry Perot scheme has many drawbacks. First, the output response is only linearly proportional to the workpiece surface velocity over a finite bandwidth. Second, the field-of-view is relatively small. Third, the Fabry Perot cavity length must be long enough so that its free spectral range is compatible with the bandwidth of the signal to be detected. This results in relatively long devices (typically longer than one foot). Fourth, servo controls are needed to properly stabilize the Fabry Perot cavity length to the correct operating (bias) point.

SUMMARY OF THE INVENTION

In view of the above problems, the present invention provides a laser-ultrasonic weld inspection system that has relatively high spatial resolution, that drastically reduces the effects of parasitic coupling, that eliminates spatial and phase aberrations imparted onto the optical read-out beam as a result of workpiece surface roughness, and that is capable of operating in on-line or off-line modes.

More specifically, a distributed source or, equivalently, an array of acoustic waves is generated in a first workpiece that has been or is being welded to a second workpiece. The acoustic waves arrive at the weld site in phase with respect to each other and, if the weld has not yet formed, are reflected from the interface between the two workpieces and illuminate the outer surface of the first workpiece. As the weld forms, an increasing portion of the acoustic waves is transmitted to the second workpiece, where they illuminate its outer surface. The acoustic waves that illuminate the outer surface of either of the workpieces (after having been transmitted through or reflected from the weld site) arrive substantially in phase with respect to each other over a locus at the outer surface and vibrate the outer surface.

The weld information acquired by the acoustic waves is read-out with a second optical beam that is reflected from the locus locations at the outer surface and is phase modulated by its vibrations. The phase modulated read-out beam is then coherently combined with a reference beam, and the resulting beat frequency is used to extract information about the weld, using either heterodyne or homodyne detection techniques.

Reading out only in-phase portions of the acoustic waves provides acoustic-wave directivity, and thereby reduces the effects of parasitic coupling. Acoustic waves that arrive at the outer surface from locations other than the weld site generate substantially out-of-phase vibrations over the outer surface and cancel out. If the acoustic-wave excitation and read-out patterns are suitably scanned, then the present invention functions as an acoustic imaging system. In general, spurious acoustic signals, including reflections and acoustic scattering from random imperfections within the workpiece or on its surface, can interfere with the detection process. In the present invention, the phased-array excitation and detection scheme significantly reduces signals from spurious noise sources, while increasing the level of the acoustic signal from the desired spatial location within, or on the surface of the workpiece.

In the preferred embodiment, a narrow annular ring-shaped pulsed optical transmitter source beam ("ping" beam) is used to generate the array of acoustic waves in the first workpiece, through either thermoelastic or ablation effects, and a narrow annular ring-shaped beam with a different diameter than the transmitter beam is used for the optical read-out beam.

Although the main function of the transmitter and receiver arrays is to provide enhanced spatial resolution, they provide secondary benefits as well. When compared to single spot laser acoustic wave generation, the array approach greatly enhances the effective available strength of the acoustic wave. One of the reasons for this enhancement arises is that the acoustic wave may be concentrated by focusing it into the area where it is needed. In addition, the laser power density may be restricted to remain in the thermoelastic regime to avoid cosmetic damage to the workpiece surface. Since the arrays permit relatively large illumination areas, the strength of the acoustic wave at the focal plane is proportionately enhanced and is mainly limited by the available laser pulse energy, rather than surface damage.

Another advantage is also realized with the array approach. If an ablative mode of acoustic wave formation is employed, then a plasma is formed by the ping laser. If the ping laser and read-out laser are incident on the same workpiece surface (single-sided operation), the ping beam and reflected read-out beam may be partially absorbed by the plasma, unless the receiver site is sufficiently spaced from the pinging site. The annular ring arrays permit the ping and read-out beams to be coaxial with different diameters. This avoids the absorption problem because there is no spatial overlap between ping and read-out beams.

The annular ring geometry also improves the quality of the acoustic waves that are generated. Many types of welders cause a substantial and variable deformation of the workpiece surface (the weld "bead"). Laser ultrasonic sources that form the acoustic waves directly below the weld bead are aberrated by the surface deformation, causing a corresponding aberration in the generated acoustic waves. With an annular ring geometry, the ring can be made larger than the deformed surface portion to avoid aberration of the ping beam, and the corresponding aberration of the acoustic waves.

The invention also compensates for phase aberrations and spatial intensity variations induced in the optical read-out beam by the optically rough vibrating surface by providing several wavefront compensation options.

The preferred option for most applications is a double-pumped phase-conjugate wavefront compensation system ("optical scrubber"). The phase-conjugate optical scrubber utilizes a double-pumped phase conjugate mirror that removes the phase and spatial intensity aberrations from the distorted read-out beam to yield a surrogate read-out beam with a clean, planar wavefront. As a result, the entire surrogate read-out beam can be coherently combined with a reference beam to dramatically improve the signal-to-noise ratio over prior laser-ultrasonic systems.

The phase-conjugate optical scrubber not only compensates for spatial phase aberrations imposed on the read-out beam by surface irregularities, it also compensates for spatial intensity aberrations imposed on the read-out beam by surface anomalies (rust spots, digs, etc.). Furthermore, the scrubber coherently sums the phase modulations induced by the surface vibrations, which is a critical requirement for coherent acoustic phased-array receiver beam formation. In addition, the phase-conjugate scrubber can "track out" whole-body motion of the workpiece, as well as differential low frequency vibrations of the workpiece (frequencies that fall within the temporal bandwidth of the optical scrubber), while preserving the desired high frequency ultrasonic response. Whole body noise sources and vibrations that are beyond the bandwidth of the scrubber can be tracked out with conventional electronic post-processing, while still preserving the desired ultrasonic signal.

A second scrubber system is an innovative adaptive optical wavefront scrubber using spatial light modulators (SLMs), such as membrane light modulators (MLMs) or liquid crystal light valves (LCLVs), configured into a closed-loop architecture. The aberrated read-out beam is reflected from the output port of the SLM, which contains a servo-controlled reflectors that planarizes the read-out beam's wavefront. A feedback loop is provided by directing a small fraction of the read-out beam, after reflection from the output port, to the input port of the SLM, where it is optically interfered with a plane-wave reference beam. The feedback loop enables the SLM to configure its 2-dimensional output port phase map so that phase distortions in the read-out beam are corrected, while global, high frequency ultrasound signals are allowed to pass through undisturbed.

A third scrubber system is similar to the second system described above, except that traditional adaptive optical 2-dimensional phase modulators (such as deformable mirrors or PZT arrays) are used in conjunction with conventional wavefront error sensors and computer algorithms that dynamically update the 2-dimensional spatial phase modulator.

All the scrubber systems that utilize SLMs are capable of tracking rapidly changing environmental distortions (such as vibrations, air turbulence, etc.), making them particularly suitable for on-line applications, such as inspection of moving parts. In addition, SLMs typically have higher photosensitivities than DPCMs. For example, the SLM can respond at its specified frame rate (typically in the range of 10 milliseconds to 100 microseconds) for an input optical intensity on the order 0.1 milliwatt per square centimeter. With image intensifiers, this sensitivity can be improved so that input intensities in the range of microwatts to nanowatts per square centimeter will suffice. Such high SLM optical sensitivities allow the present ultrasonic inspection system to be used for evaluation of workpieces with very low surface reflectivities and/or with extremely low optical damage thresholds.

These and other features and advantages of the invention will be apparent to those skilled in the art from the following detailed description of preferred embodiments, taken together with the accompanying drawings, in which:

BRIEF DESCRIPTION OF THE DRAWINGS

FIG. 1c is a sectional view of a welded workpiece illustrating the effect of a parasitic acoustic coupling source on the ultrasonic probe beam of FIG. 1a.

FIG. 4a a schematic diagram of a wavefront compensated interferometer embodiment utilizing a double-pumped phase conjugator (DPCM).

DETAILED DESCRIPTION OF THE INVENTION

Figure 1A:
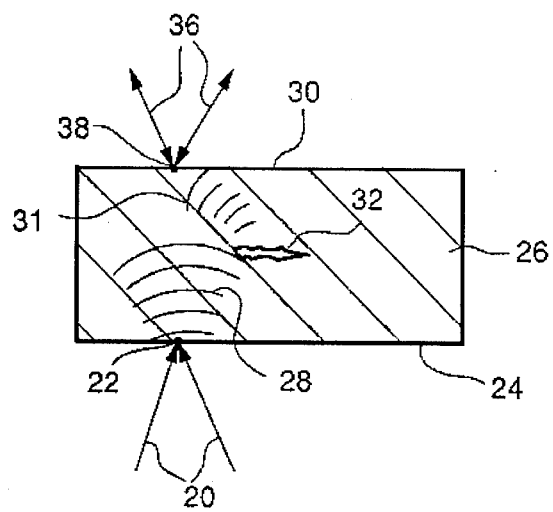
FIG. 1a, described above, is sectional view of a prior weld inspection technique in which a welded workpiece is being probed by an ultrasonic beam.
Figure 1B:
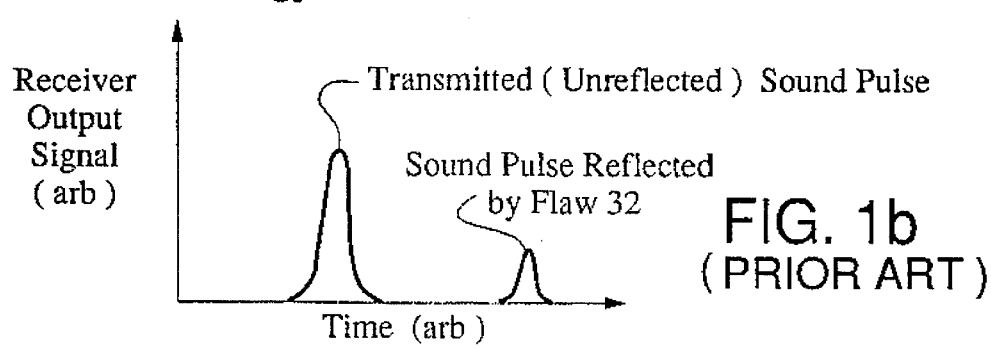
FIG. 1b is a graph corresponding to FIG. 1a, of an inspection output signal as a function of time.
Figure 1C:
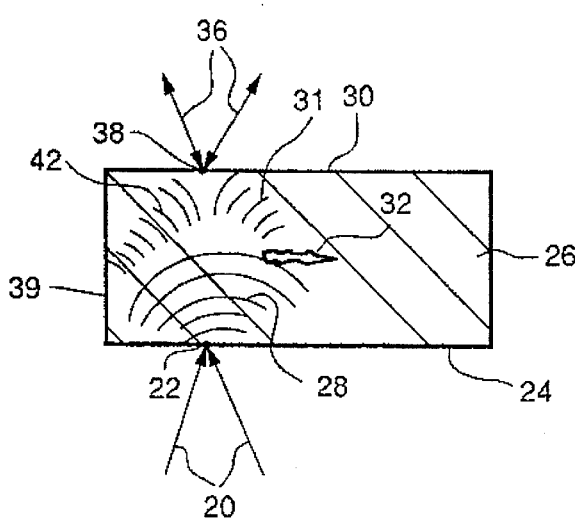
Figure 1D:
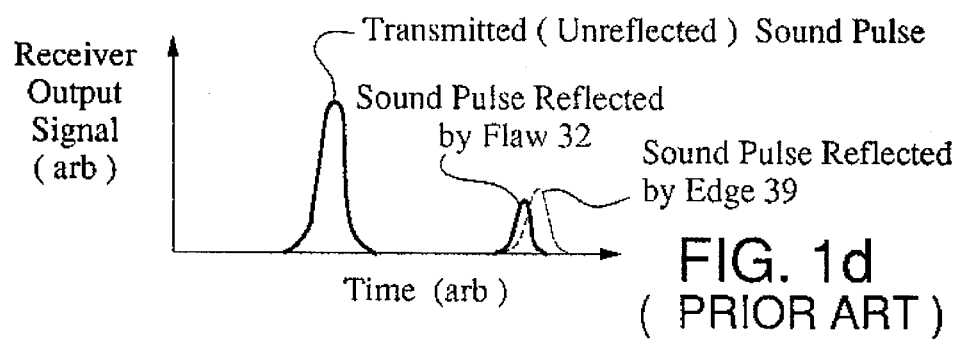
FIG. 1d is a graph corresponding to FIG. 1c, of an inspection output signal as a function of time.
Figure 2A:
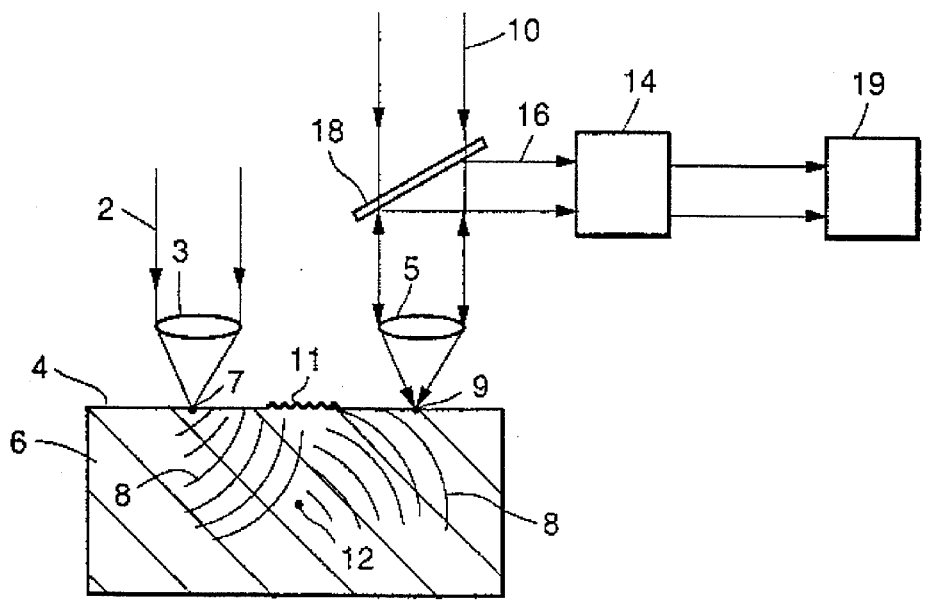
FIG. 2a is a block diagram of a single-sided laser-ultrasonic weld inspection system constructed in accordance with the present invention.
Figure 2B:
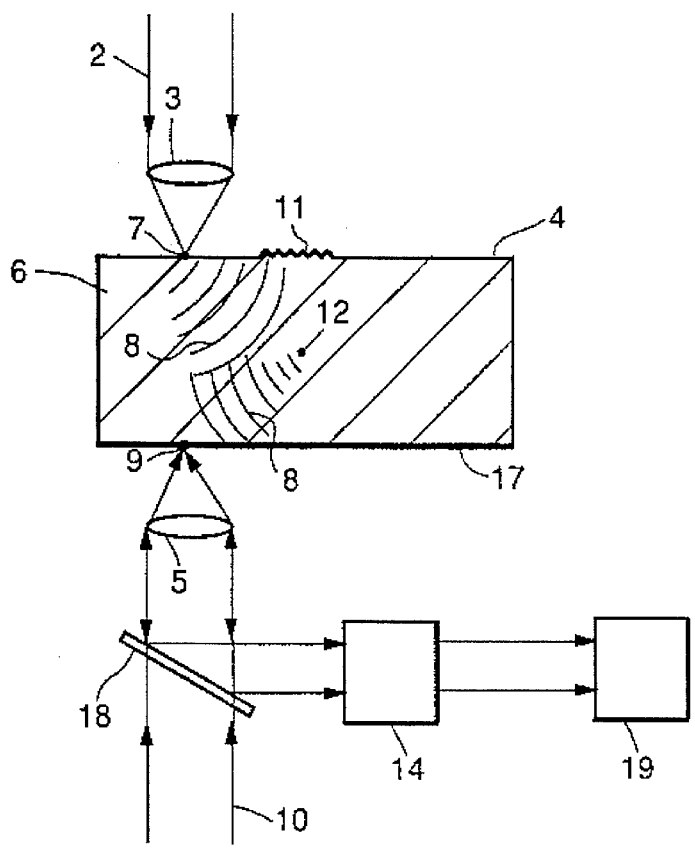
FIG. 2b is a block diagram of a double-sided laser-ultrasonic weld inspection system constructed in accordance with the present invention.

FIGS. 2a and 2b illustrate the general principles of the invention. As illustrated in FIG. 2a, it generally consists of a laser acoustic source beam ("pinger" beam) 2 that is focused by a lens 3 to form a spatial light pattern 7 on the surface 4 of a workpiece 6 for generating an array of acoustic waves (an acoustic probe beam) 8 in the workpiece 6, a read-out beam 10 that is focused by a lens 5 to form a second spatial light pattern 9 on the workpiece surface 4 for detecting the acoustic probe beam 8 after it have probed an inspection site 12 in the workpiece 6, such as a weld or flaw 12, and signal processor 19 for extracting information about the weld or flaw 2 from the phase modulated reflected read-out beam 16. In the preferred embodiment, a read-out beam wavefront compensator 14 is used to compensate for the phase and amplitude aberrations imparted onto the reflected read-out beam 16 by the workpiece surface 4. The reflected read-out beam 6 is directed to wavefront compensator 14 and signal processor 19 by beam director 18, preferably a beam splitter.

FIG. 2a illustrates a configuration in which the pinger beam 2 and read-out beam 10 are incident on the same workpiece surface 4. FIG. 2b illustrates a configuration in which the pinger and read-out beams are incident on different workpiece surfaces, preferably a workpiece surface 17 that is opposite the surface 4 that the pinger beam 10 is focused on.

In addition to the two beam configurations illustrated in FIGS. 2a and 2b, there are several types of read-out beam compensators 14 that may be used, as will be discussed below. The best combination of beam configurations and read-out beam compensators is dependent on the particular application.

For small area pinger beam spatial light patterns 7 it is preferable to offset the light pattern 7 from the area being probed 12 so as to avoid damaged surface areas 11 (such as areas damaged by the welding beam). However, as a consequence of the distributed nature of the spatial light pattern 7, large offsets require that the acoustic beam 8 propagate at large angles to the workpiece surface 4 normal. Large propagation angles can degrade temporal resolution unless the spatial light pattern 7 width, projected in a direction parallel to the propagation of the acoustic probe beam 8, is much smaller than 1 mm. By lens 3 a cylindrical lens, one can minimize this spatial light pattern width and avoid the problem of air breakdown that can result from focusing to small spot sizes with conventional lenses. In some cases, it is also preferable to offset the receiver spatial light pattern 9, to further discriminate against spurious acoustic signals. However, to avoid degradation in temporal resolution, the same spatial light pattern width restrictions apply. Specific preferred spatial light pattern shapes will be discussed in more detail below.

Figure 3:
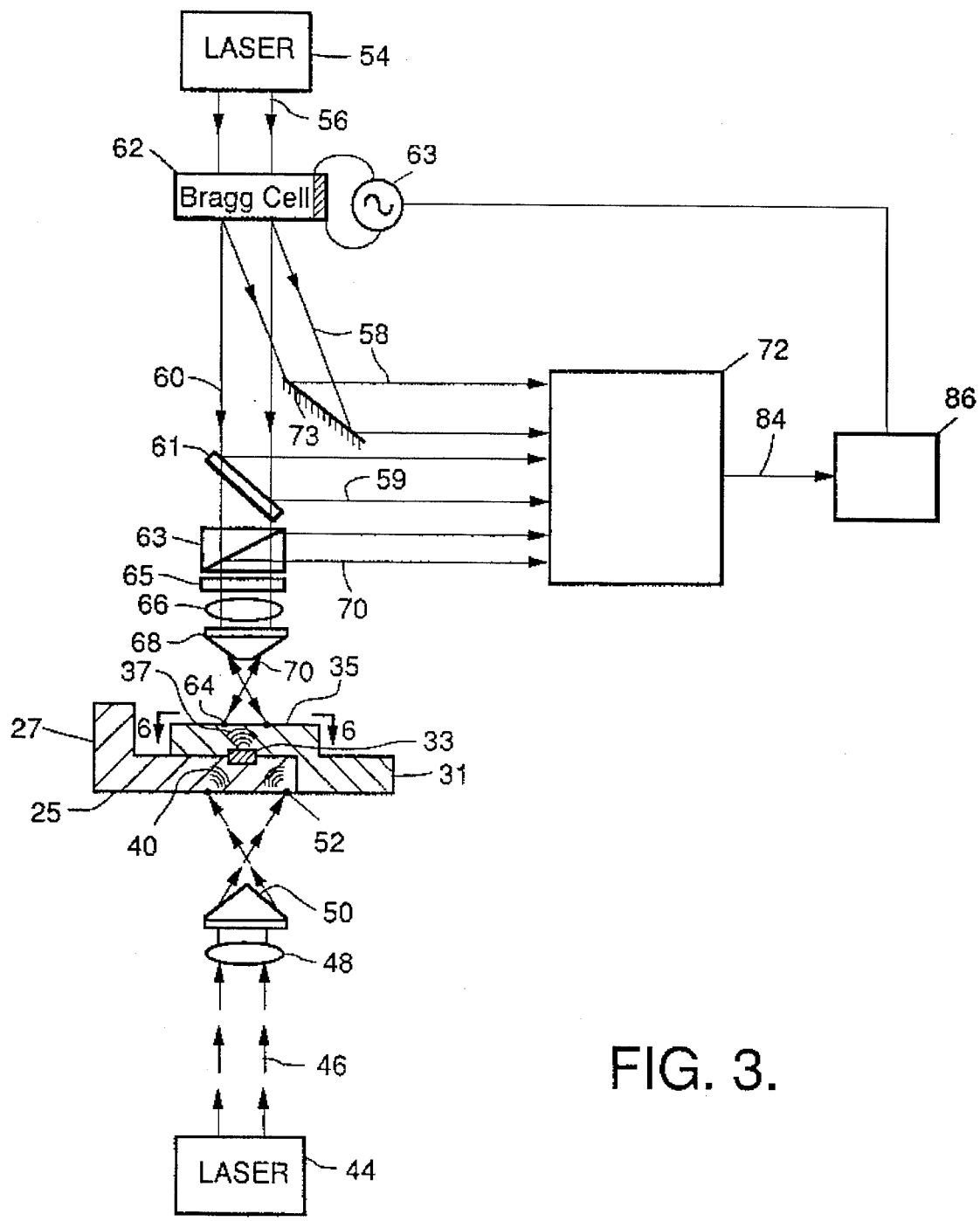
FIG. 3 is a cross-sectional schematic diagram of a laser-ultrasonic weld inspection system for off-line operation.

A preferred embodiment for off-line inspection of relatively small size workpieces is illustrated in FIG. 3. For illustration purposes, the invention will be described in the context of a weld inspection application, wherein a "keystone" weld bridge 33 is located between two metal workpieces 27 and 31. It is assumed that the quality of the weld 33 is ascertainable by measuring its diameter.

A pulsed transmitter laser 44 generates a pulsed beam 46 that is focused by a lens 48 and axicon 50 to form a spatial light pattern 52, such as a "ring" pattern, on the surface 25 of one of the welded workpieces 27. The spatial light pattern 52 generates an array of acoustic waves 40 through either thermoelastic effects or through ablation of material from the surface.

For operation in the thermoelastic regime the power density of the pulsed beam 46 at the surface 25 should be kept below approximately 10 MW/cm$^2$. At such power densities, the acoustic waves 40 are generated by the thermoelastic stresses and strains that are induced by localized heating of the material. The main advantage of operating in the thermoelastic regime is that the material is not damaged by the pulsed beam 46.

It is also possible to operate in the ablation regime by keeping the power density of the pulsed beam 46 above 10 MW cm$^2$. In the ablation regime, material is ablated from the surface 25, producing a net reaction force against the surface 25. This force produces a stress at the surface which in turn generates compression-mode acoustic waves 40. The advantage of operating in this power regime is that the acoustic waves 40 produced via ablation are stronger than those produced via thermoelastic effects. The main disadvantage is that the material is damaged at or near the surface 25 through the ablation process.

The acoustic waves 40 propagate through the first workpiece 27, arrive in phase at the weld 33 and are coupled into the second workpiece 31 through the weld 33. The acoustic waves 40 then propagate through the second workpiece 31 and vibrate its outer surface 35. The acoustic waves 40 arrive substantially in phase over an annular ring locus at the outer surface 35.

The vibrating surface is then probed interferometrically. This is accomplished by using a second laser 54, preferably a continuous-wave (CW) or long-pulse laser, to generate a second optical beam 56 which is subsequently divided into a diffracted reference beam 58 and an undiffracted read-out beam 60 by a Bragg cell 62 that is driven by an rf power source 63. The diffracted reference beam 58 is shifted in frequency by Bragg cell 62 and directed to a combination wavefront compensator/interferometer 72 (wavefront compensated interferometer) by mirror 73. The undiffracted read-out beam 60 is used to read-out the acoustically induced displacement of surface 35.

The intensity of read-out beam 60 is preferably much higher than the intensity of diffracted reference beam 58. This way, the rf power required to drive Bragg cell 62 is relatively low, which reduces the potential for rf electrical interference in the processing electronics 86. A high intensity read-out beam 60 is also preferable in order to help overcome the low optical reflectivity and/or high optical scattering that are typically exhibited by workpieces.

The read-out beam 60 passes through a beam splitter, 61 that splits a portion of the read-out beam into an optional compensator input beam 59. The use of the optional input beam 59 will depend on the type of wavefront compensator used. For DPCM and conventional adaptive optics compensators, beam 59 is not used. For light valve compensators, which typically have high sensitivity, only a few microwatts of power is required in beam 59. The function of beam 59 will be explained in more detail below.

The read-out beam 60 then passes through a polarizing beamsplitter 63, that is oriented to transmit the read-out beam 60, and through a quarter-wave plate 65, which converts the read-out beam's linear polarization to circular polarization. The read-out beam 60 is then focused by a lens 66 and axicon 68 to form a spatial light pattern 64, preferably a ring-shaped pattern, on the vibrating surface 35 over the locus. The geometry and function of the transmitter ring 52 and read-out ring 64 will be discussed below.

A portion of the read-out beam 60 is reflected and is phase-modulated by the vibrating surface 35. The modulated read-out beam 70 is then collected by the lens 66 and axicon 68 and directed back through quarter-wave plate 65, where its circular polarization is converted back a linear polarization that is orthogonal to its original linear polarization. The linearly polarized modulated read-out beam 70 is reflected by polarizing beamsplitter 63 and directed to wavefront compensated interferometer 72.

The preferred intensity ratio between the read-out beam 60 and the reference beam 58 is also dependent on the type of wavefront compensator that is used in interferometer 72. With a DPCM wavefront compensator, the intensity ratio is preferably chosen so that the intensity of reference beam 58 and modulated read-out beam 70 are approximately equal. This enhances the response speed of the DPCM.

The wavefront compensated interferometer 72 removes any spatial phase aberrations induced on the modulated read-out beam 70 as a result of its reflection from the optically rough vibrating surface 35, coherently combines it with reference beam 58 and generates an electronic beat frequency signal. The beat frequency signal 84 is sent to a processor 86 which analyzes the beat frequency to extract information about the weld 33.

For moderate speed applications, the preferred wavefront compensator for use in the wavefront compensated interferometer 72 is the double or triple-pumped phase conjugate mirror. Preferred double-pumped phase conjugate mirror (DPCM) embodiments are illustrated in FIGS. 4a–4d. For some examples of general laser beam cleanup using double-pumped phase conjugate mirrors, see U.S. Pat. No. 4,991, 177, entitled "LASER BEAN CLEAN-UP USING MUTUALLY PUMPED PHASE CONJUGATION", issued Feb. 5, 1991 to T. Y. Chang, et al., and U.S. Pat. No. 4,911,537, entitled "BIRD-WING PHASE CONJUGATION USING MUTUALLY INCOHERENT LASER BEAMS", issued Mar. 27, 1990 to M.D. Ewbank.

The primary function of the DPCM is to remove spatial and intensity aberrations induced on the modulated read-out beam 70 as a result of its reflection from the optically rough vibrating surface 35. A DPCM with a single commercially available photorefractive crystal 148 is more cost effective than the light valve embodiments described below. Furthermore, since thick volume holograms are written in the photorefractive crystal 148, the diffraction efficiency is much higher than the relatively thin holograms written in ferroelectric light valves. Another advantage of the DPCM embodiment over light valve embodiments is that some of the DPCM configurations permit auto alignment of the reference beam 58 with the modulated and compensated read-out beam 176. Thus, the two beams exactly overlap at detectors $D_1$ and $D_2$.

For many applications, the preferred embodiment of a wavefront compensated interferometer 72 using a DPCM is illustrated in FIG. 4a. Reference beam 58 is split by beamsplitter 77 into a compensator reference beam 79 and a detector reference beam 81. The compensator reference beam 79 passes through a polarizing beamsplitter 83 that is oriented to transmit the beam's linear polarization, and through a Faraday rotator 75, which rotates its linear polarization by 45 degrees. The compensator reference beam 79 is then focused into the +c-face 85 of a photorefractive crystal 148 by lens 87. The photorefractive crystal is preferably $BaTiO_3$, but it could also be $Ba_{2-x}Sr_xK_{1-y}Na_yNb_5O_{15}$, $KNbO_3$, $Sr_{1-x}Ba_xNb_2O_6$ or any other photorefractive crystal. In addition, the double-pumped phase conjugator implementation is not limited to a photorefractive crystal. Other types of nonlinear materials could be used in place of the photorefractive crystal.

The modulated read-out beam 70 is focused into an a-face 89 of the crystal 148 by lens 91, where it combines with the compensator reference beam 79 to write mutual photorefractive index gratings (not shown). The modulated read-out beam 70 diffracts off the mutual gratings and emerges as a clean (scrubbed) compensated read-out beam Compensated read-out beam 71 is actually the phase-conjugate of the compensator reference beam 79, so it has the same frequency, wavefront and polarization as the compensator reference beam 79 The compensated read-out beam 71 passes through Faraday rotator 75, which rotates its polarization by another 45 degrees. Since the compensated read-out beam's polarization is now orthogonal to the polarization of the compensator reference beam 79, it is reflected by polarizing beamsplitter 83 towards interferometric beamsplitter 93, preferably a 50/50 beamsplitter. The portion of beam 71 that is transmitted through beamsplitter 93 is combined, in angular registration, with the portion of beam 81 that is reflected by beamsplitter 93. The combined beams 95 are focused into detector $D_1$ by lens 97. Detector $D_1$ detects the beat frequency between the combined beams 95 and produce an output electronic signal with a spectrum that is centered on an intermediate output frequency $f_1$.

Similarly, the portion of compensated read-out beam 71 that is reflected by beamsplitter 93 is combined, in angular registration, with the portion of beam 81 that is transmitted by beamsplitter 93. These combined beams 97 are focused into detector $D_2$ by lens 99. Detector $D_2$ detects the beat frequency between the combined beams 95 and produce an output electronic signal with a spectrum that is centered on an intermediate output frequency $f_1$. The phase modulations on the portions of beam 71 that are transmitted and reflected by beamsplitter 93 are 180 degrees out of phase with respect as a consequence of reflection and transmission from the beamsplitter. However, amplitude variations (possibly due to laser instability) are not phase shifted by beamsplitter 93.

$D_1$ and $D_2$'s output signals are sent to a differential amplifier 101, which performs a differencing operation on the two detector output signals. Amplitude fluctuations that are present in both detectors' output signals are not 180 degrees out of phase, and therefore cancel. Since the phase modulations (from the signal of interest) in detector output are 180 degrees out of phase with respect to each other, they are doubled by the differential amplifier 101. The output 84 of the amplifier 101 is sent to processor 86 (shown in FIG. 3) for extracting information about the weld from the beat frequency. Existing electronic post-processing techniques (phase-locked loops, tracking circuits, etc.) can be used to compensate for acoustic vibrations, which are typical in a manufacturing environment.

Figure 4B:
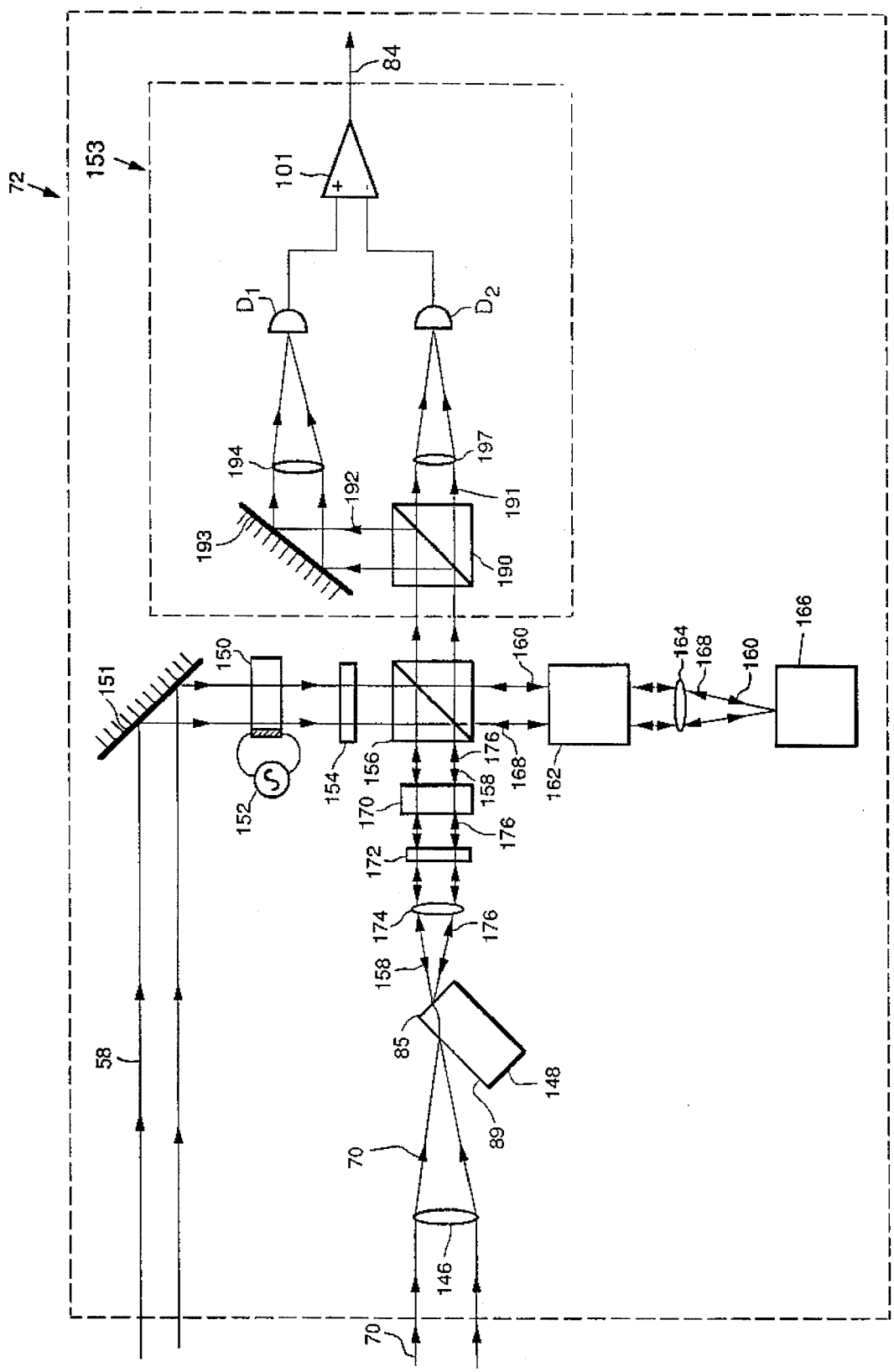
FIG. 4b is a schematic diagram of a DPCM wavefront compensated interferometer embodiment utilizing a self-aligning PCM.

One limitation with the wavefront compensated interferometer embodiment of FIG. 4a is that it is not self-aligning. The angles and positions of most elements must be carefully adjusted and controlled. A self-aligning DPCM wavefront compensated interferometer is illustrated in the embodiment of FIG. 4b. Mirror 151 directs reference beam 58 to a frequency shifter, preferably a Bragg cell 150 that is driven by an AC voltage source 152, that imparts a frequency shift of between 20 and 40 MHz on beam 58. This allows the signal monitor 153 to operate in a heterodyne mode. Reference beam 58 is then passed through a variable half-wave plate 154 and is directed to a first polarizing beamsplitter 156. The polarizing beamsplitter 156 splits the reference beam into a compensator reference beam 158 and a detector reference beam 160 by reflecting the vertical polarization component of the reference beam 58 and transmitting its horizontal polarization component. The portions of the original reference beam 58 that go into the compensator reference beam 158 and the detector reference beam 160 can be controlled by varying the angle of the half-wave plate 154. For example, if the half-wave plate 154 is adjusted so that the reference beam 58 has a 45 degree linear polarization, then half the power in the reference beam 58 will go to the compensator reference beam 158 and half will go to the detector reference beam 160 (assuming no absorption losses).

The detector reference beam 160 passes through a Faraday rotator 162, which rotates its polarization by 45 degrees. The beam is then focused by a lens 164 into a second phase-conjugator 166, preferably a self-pumped phase conjugator implemented with a second photorefractive crystal. The phase-conjugate mirror 166 generates a phase-conjugate 168 of the detector reference beam 160 which counter-propagates back through the Faraday rotator 162 where its polarization is rotated by 45 degrees (making the polarization of the phase-conjugate detector reference beam 168 vertical), and back to polarizing beamsplitter 156, which reflects beam 168.

The compensator reference beam 158 passes through a second Faraday rotator 170, which rotates its vertical polarization by 45 degrees. It then passes through a second half-wave plate 172, which rotates its polarization by another 45 degrees (making the polarization horizontal), and is focused by a lens 174, preferably a cylindrical lens, into the +c-face 85 of photorefractive crystal 148.

The modulated read-out beam 70 is focused into an a-face 89 of crystal 148 by lens 146. Beams 70 and 158 write mutual photorefractive index gratings (not shown) in the photorefractive crystal 148. The temporally modulated read-out beam 70 diffracts off the mutual gratings to form the phase-conjugate of the compensator reference beam 176, and the compensator reference beam 158 diffracts off the mutual gratings to form the phase-conjugate of the modulated read-out beam (not shown). This cross-readout process results in the temporal phase modulations of the modulated read-out beam 70 (induced by reflection from the vibrating surface) being coupled over to the phase-conjugate compensator reference beam 176 without a corresponding coupling of the spatial phase aberrations (or intensity drop-outs) imparted on the modulated read-out beam 70 by reflection from the optically rough or imperfect surface of the welded workpiece (not shown). The result is a phase-conjugate compensator reference beam 176 that has both the desired temporal modulation of the modulated read-out beam 70 and the clean wavefront of the compensator reference beam 158.

The phase-conjugate compensator reference beam 176 counter-propagates with respect to the compensator reference beam 158. It passes back through the lens 174 and through the half-wave plate 172, which rotates its horizontal polarization by −45 degrees. The polarization rotation is −45 degrees because the phase-conjugate compensator reference beam 176 is a "time-reversed" replica of the compensator reference beam 158 and the half-wave plate 172 is a reciprocal optical element. The Faraday rotator 170 rotates the polarization of the phase-conjugate compensator reference beam 176 by +45 degrees so that the polarization is now horizontal again (the Faraday rotator 170 is a non-reciprocal optical element). This allows the beam to pass through the polarizing beam splitter 156. The combined phase-conjugate compensator reference beam 176 and phase-conjugate detector reference beam 168 are then directed to the signal monitor 153 for detection of the beat-frequency between them.

Beams 176 and 168, after passing through and reflecting off (respectively) polarizing beamsplitter 156 are orthogonally polarized. In order to coherently combine these beams for heterodyne detection, the pair of beams are directed to a second polarizing beamsplitter 190 that is rotated 45 degrees with respect to polarizing beamsplitter 156. Beamsplitter 190 functions as an interferometric beam combiner, so that the pair of beams, 191 and 192, that emerge from beamsplitter 190 each contain coherent contributions of the original input beams 176 and 168. By conservation of energy, beams 191 and 192 each contain the desired phase-difference information of input beams 176 and 168, but are 180 degrees out of phase with respect to each other. Beams 191 and 192 are then directed into separate optical detectors $D_1$ and $D_2$ by mirror 193 and lenses 194 and 197. The electrical outputs of detectors $D_1$ and $D_2$ are sent to differential amplifier 101 that performs the same differencing function described above in connection with FIG. 4a. The differential amplifier output 84 is directed to processor 86 (not shown) for demodulation. Signal monitor 153 functions as a balanced detection circuit, with common-mode rejection of additive noise, but with twice the signal level for the desired output signal information, due to the 180 degree phase shift between beams 191 and 192, coupled with the differencing function of differential amplifier 101.

Figure 4C:
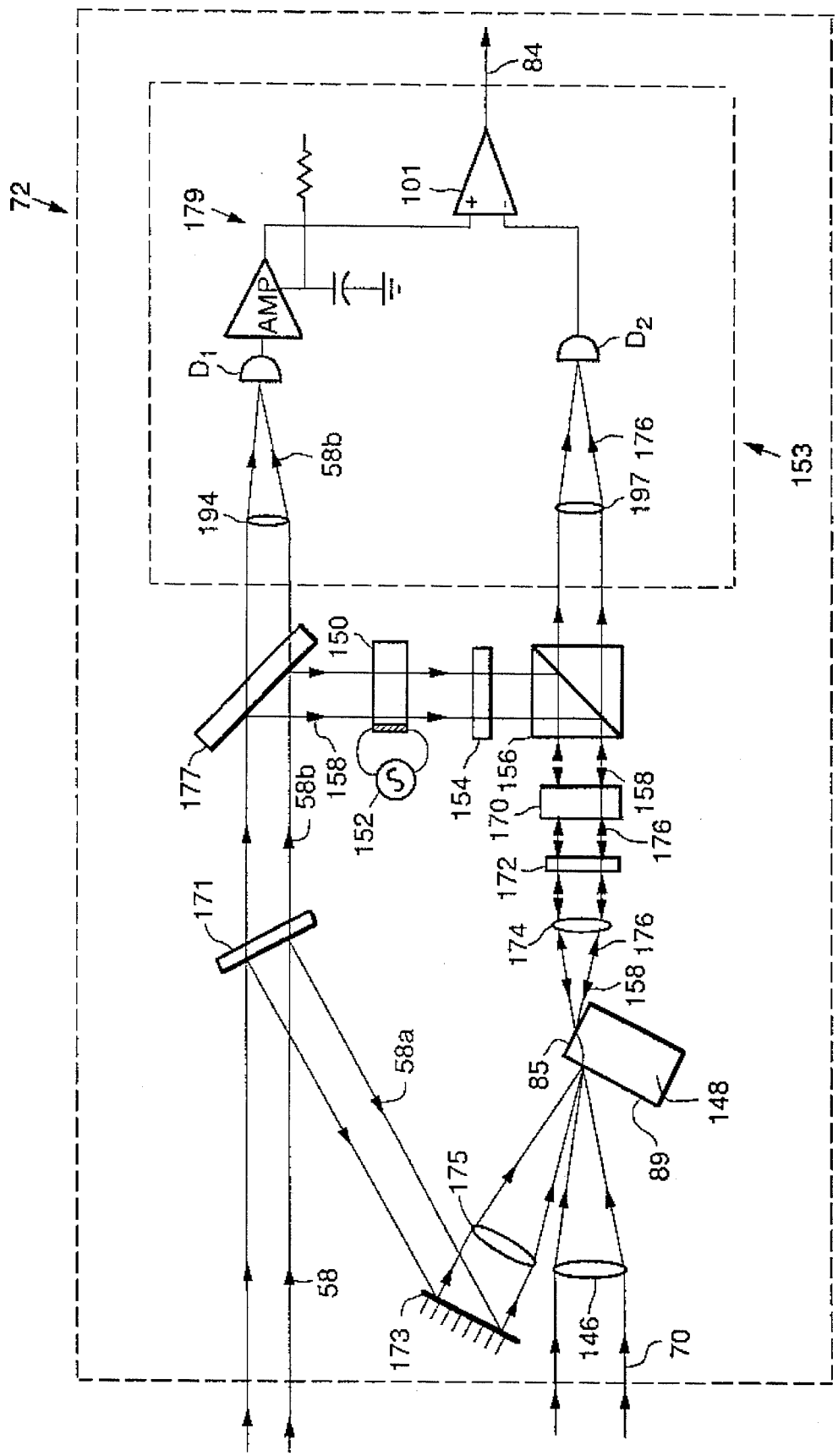
FIG. 4c is a schematic diagram of a wavefront compensated interferometer embodiment utilizing a self-aligning triple-pumped phase-conjugate mirror (TPCM).

FIG. 4c illustrates an alternative wavefront compensated interferometer embodiment that is also self-aligning, and that employs a triple-pumped phase-conjugate mirror (TPCM). The embodiment of FIG. 4c is a variation on the embodiment of FIG. 4b, and common elements are labeled with the same element numbers. The main differences between the embodiments of FIGS. 4b and 4c is the use of an additional pump beam 58a derived from reference beam 58, and the use of a different type of signal monitor 153. Pump beam 58a is split out of reference beam 58 by beamsplitter 171 and directed to the a-face of the crystal 148 by mirror 173 and lens 175. Beam 176 is the phase conjugate of compensator reference beam 158 and consists of two co-aligned beams at the input frequencies of modulated read-out beam 70 and reference beam 58. If the compensator reference beam 158 is unaberrated, then the phase conjugate beam 176 is also. However, even if small aberrations are present on beam 158, they will appear in both of the two co-aligned beams (that have the frequencies of beams 70 and 58) that make up the phase conjugate beam 176. Since the aberrations appear in both of the co-aligned beams, their wavefronts will be matched and high detection efficiency will result. Note that the TPCM, like the DPCM, works most efficiently if no one of the three input beams 58a, 70 and 158 form internal gratings via cross beats between any other input beam. For this reason, Bragg cell 150 is used to offset beam 158 in frequency from beams 58a and 70. The frequency difference between any pair of input beams should preferably exceed the inverse of the grating formation time.

One drawback to the embodiment of FIG. 4c is that signal monitor 153 is not a balanced detector like the ones used in the embodiments of FIGS. 4a and 4b. However, laser amplitude noise can still be canceled. A beamsplitter 177 is used to split reference beam 58 into reference beam portion 58b and compensator reference beam 158. Lens 154 focuses reference beam portion 58b into detector $D_1$. The two co-aligned beams (that have the frequencies of beams 70 and 58) that make up beam 176 are focused into detector $D_2$ by lens 197. In this scheme, detector $D_1$ is a direct detector and detector $D_2$ is a heterodyne detector. Laser amplitude noise is equally present on both detector signals and, if the input optical signals are equal in magnitude, subtracting the detector outputs with differential amplifier 101 cancels the laser amplitude noise. An automatic gain control (AGC) circuit is used at the output of detector $D_1$ to balance the magnitude of the detector signals.

An advantage of the embodiment of FIG. 4c, results from the temporal response properties of the TPCM. The temporal response to a perturbation of an existing grating system in the crystal 148, which results in a partial set of new gratings being formed, is much faster than the time to build up the gratings from a dark state. Therefore, the reference beam 58a input can maintain a grating system during read-out beam 70 intensity drop-outs, which speeds up the acquisition of the correct gratings when the read-out beam 70 re-appears, subject to incoherent erasure of the gratings by the various input beams.

In applications which require very high temporal resolution, it is advantageous to use correspondingly higher offsets between read-out and reference beam frequencies to produce higher intermediate frequencies out of the heterodyne detectors. A preferred method of achieving these frequency offsets is to employ a double-pass Bragg cell configuration, as illustrated in the wavefront compensated interferometer embodiment of FIG. 4d. Compensator reference beam 158 is split into two equal intensity beams 158a and 158b by Bragg cell 150. The undiffracted component 158a is the reference beam of the DPCM, whose phase-conjugate reflection 176 carries the modulated read-out beam's 70 phase modulation (as in the embodiments of FIGS. 4b and 4c). The diffracted portion 158b is frequency upshifted by the Bragg cell driving frequency $f_2$. It is reflected by mirror 166, which is preferably a phase-conjugate mirror into which beam 158b is focused by lens 164. However, mirror 166 may also be a corner reflector or a "cat's eye" retroreflector. The reflected beam 159 returns to Bragg cell 150, where it is again split into a diffracted beam 159' and undiffracted beam 159". The undiffracted beam 159" (which retains the single frequency upshift $f_2$) is reflected by mirrors M2 and M3 and is focused onto detector $D_2$ by lens 197. The diffracted beam 159' is again upshifted in frequency (for a total frequency shift of $2f_2$) and, after polarization rotation, is focused onto detector $D_1$ by lens 194.

Similarly, beam 176 is split into a diffracted beam 176' (downshifted in frequency by $f_2$) and an undiffracted beam 176". The diffracted beam 176' is parallel to beam 159" (which has a frequency upshift of $f_2$) and is also focused onto detector $D_2$ by lens 197. Thus, the beat frequency out of detector $D_2$ is equal to $2f_2$. The undiffracted beam 176" is parallel to diffracted beam 159' (which has a frequency upshift of $2f_2$) and is also focused onto detector $D_1$. Thus, the beat frequency out of detector $D_1$ is also equal to $2f_2$.

Figure 4D:
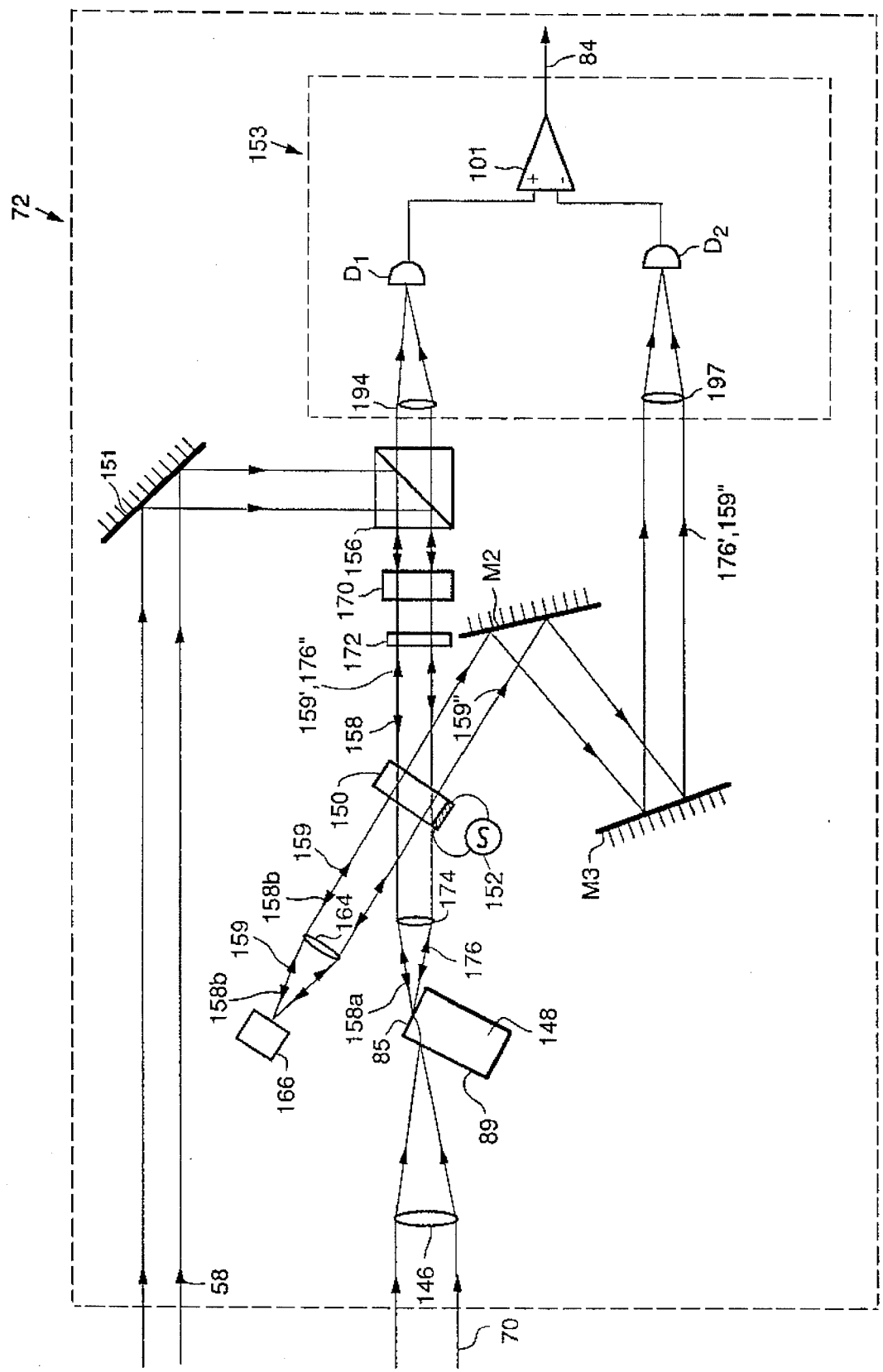
FIG. 4d a schematic diagram of a wavefront compensated interferometer embodiment utilizing a DPCM and a double-pass Bragg cell configuration.

A secondary advantage of the embodiment of FIG. 4d is that the Bragg cell driver 152 at frequency $f_2$ cannot effectively couple electrical noise into the outputs of detectors $D_1$ and $D_2$. Although the common-path error cancellation feature found in the embodiment of FIG. 4c is not available in this embodiment, the system is substantially self-aligning. Furthermore, laser amplitude noise is effectively canceled by the same balanced signal monitor 153 found in the embodiment of FIG. 4a.

The beat frequency output 84 of the differential amplifier 101 in all of the wavefront compensated interferometer embodiments discussed above are amplified and phase detected by processor 86 to yield an electronic pulse whose output shape and intensity yields the desired measure of the weld size and quality.

Although the DPCM and TPCM-based wavefront compensated interferometers of FIGS. 4a–4d are generally preferred for off-line applications, on-line in-situ applications often require higher speed operation than can be provided by existing DPCMs and TPCMs. Alternative wavefront compensators are available which are capable of sub-millisecond response speeds and higher sensitivities, as will be described next. Many of the high-speed compensators that can be employed in the wavefront compensated interferometer are described in the context of adaptive-optics imaging. For the present ultrasonic inspection system, different geometries that those described for adaptive optics imaging are required, as is described below.

Figure 5A:
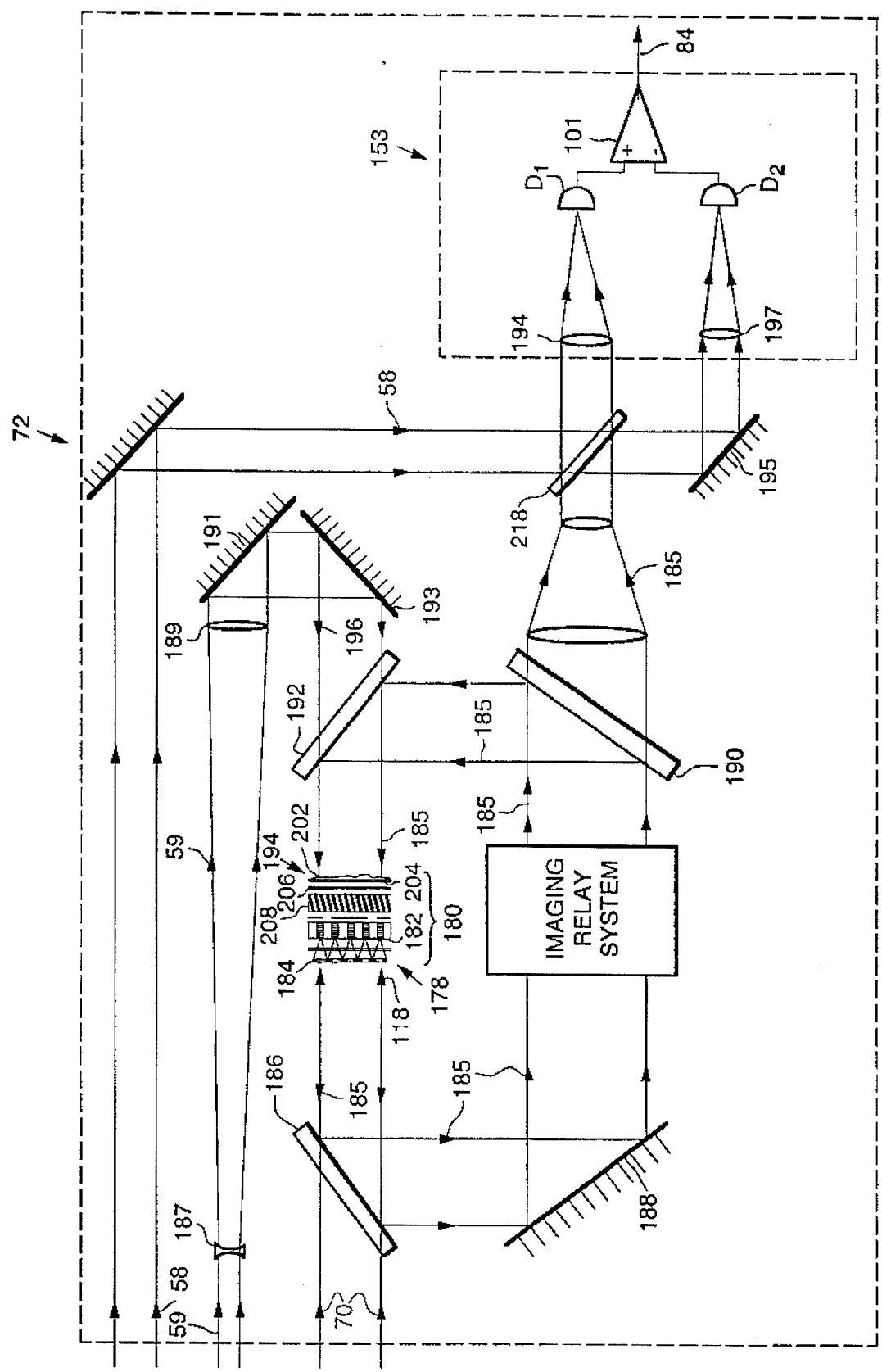
FIG. 5a is a schematic diagram of a wavefront compensated interferometer embodiment utilizing a membrane-based spatial light modulator (MLM).
Figure 5B:
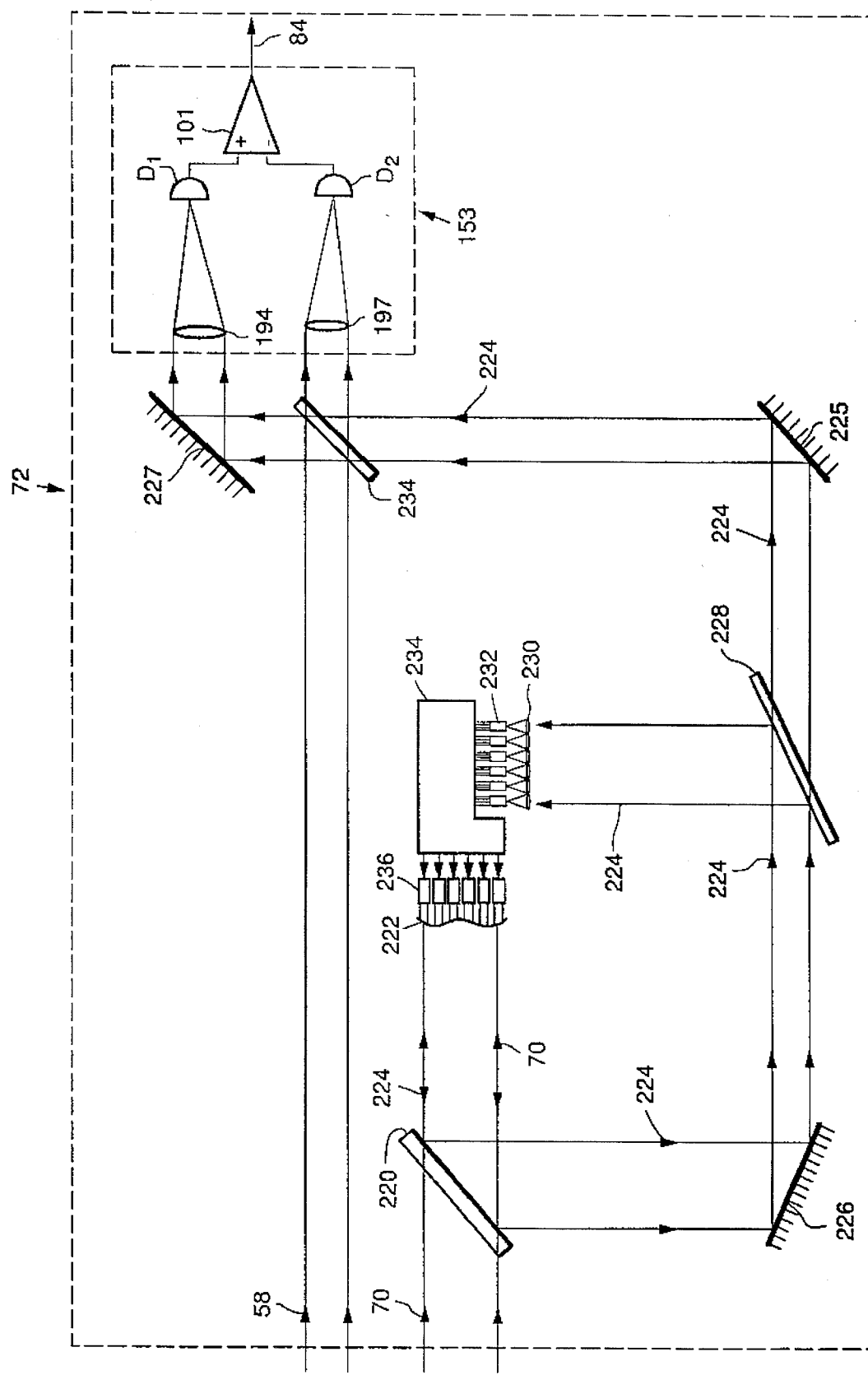
FIG. 5b a schematic diagram of a wavefront compensated interferometer embodiment utilizing "traditional" adaptive optics.

One approach is to use refracting/reflecting (closed loop) adaptive optics, as illustrated in the wavefront compensated interferometer embodiments of FIGS. 5a and 5b. In FIG. 5a, high speed compensation is achieved with a compensating deformable mirror realized as membrane-based spatial light modulator 180 (MLM), which utilizes an array 182 of discrete membrane micro-mirrors that are driven by a microchannel plate current amplifier 208. A detailed description of this wavefront compensation system can be found in Celestino J. Gaeta et al., "Characteristics of Innovative Adaptive-Optics Servos That Use Membrane-Based Spatial Light Modulators", *J. Opt. Soc. Am. A*, vol. 11, No. 2, pages 880–894 (1994).

The temporally modulated read-out beam 70 is directed to the read-out side 178 of a membrane-based spatial light modulator 180. A lens array 184 focuses the modulated read-out beam 118 onto a reflective membrane array 182, where it is retro-reflected. The retro-reflected modulated read-out beam 185 is then partially reflected by a beam splitter 186 and is directed by a mirror 188 to a second beam splitter 190. The second beamsplitter transmits part of the retro-reflected read-out beam 185 to beam splitter 218 and reflects the rest towards a third beam splitter 192, which directs the beam to the write side 194 of the spatial light modulator 180.

Reference beam 59 is expanded by lenses 187 and 189 and directed to the write side 194 of the spatial light modulator 180 by mirrors 191 and 193, where it optically interferes with the retro-reflected modulated read-out beam 185. This creates an interference pattern 202 on the photocathode surface 204 of the light modulator 180. The modulated read-out beam 70 that reflects from the membrane array 182 on the read-out side of the light valve 178 experiences a phase shift that corresponds to the interference pattern on the write side 194 of the light modulator 180. Since a portion of the retro-reflected, temporally-modulated and phase-corrected read-out beam is directed to the write side 194 to interfere with reference beam 59, a feedback loop exists. After multiple iterations, the retro-reflected, temporally-modulated read-out beam 185 is substantially free from spatial-phase aberrations (wavefront compensated).

Reference beam 58 is directed to a beamsplitter 218, where it is where it combines with beam 185. The combined beams are directed to lenses 194 and 197 (with mirror 195) of signal monitor 153 for detection of the resulting beat-frequency. Although the MLM cannot compensate as much of the speckled field (arising from scattering off rough workpiece surfaces) as a phase conjugator, it need not accommodate a large number of compensation sites in order to be effective. Furthermore, it offers an optical efficiency advantage over phase conjugators because the micro-mirror array 182 reflectivity is over 95%, compared to 40%–50% for DPCMs and TPCMs, and 20% for real-time holograms.

In the wavefront compensated interferometer embodiment of FIG. 5b, a "traditional"adaptive optics system is used for wavefront compensation. The modulated read-out beam 70 is directed through a first beam splitter 220 and to a deformable mirror 222, which retro-reflects the beam 70. The retro-reflected read-out beam 224 is then directed by the first beamsplitter 220, a mirror 226, and a second beam splitter 228 to a two-dimensional lens array 230. The lens array 230 focuses the retro-reflected read-out beam 224 onto a two-dimensional array of quadrant detectors 232 that sense the wavefront error on that part of the beam. The signals from the quadrant detectors 232 are sent to a processor 234 and are used to adjust the voltage levels across piezoelectric actuators 236 in a manner that causes the deformable mirror 222 deflection to minimize the wavefront error in the retro-reflected read-out beam 224. The portion of beam 234 that passes through beamsplitter 228 is directed to a third beamsplitter 234 by mirror 225, where it combines with reference beam 58. The combined beams are directed to lens 197 and lens 194 (by mirror 227) of signal monitor 153, for detection of the resulting beat-frequency.

Figure 6:
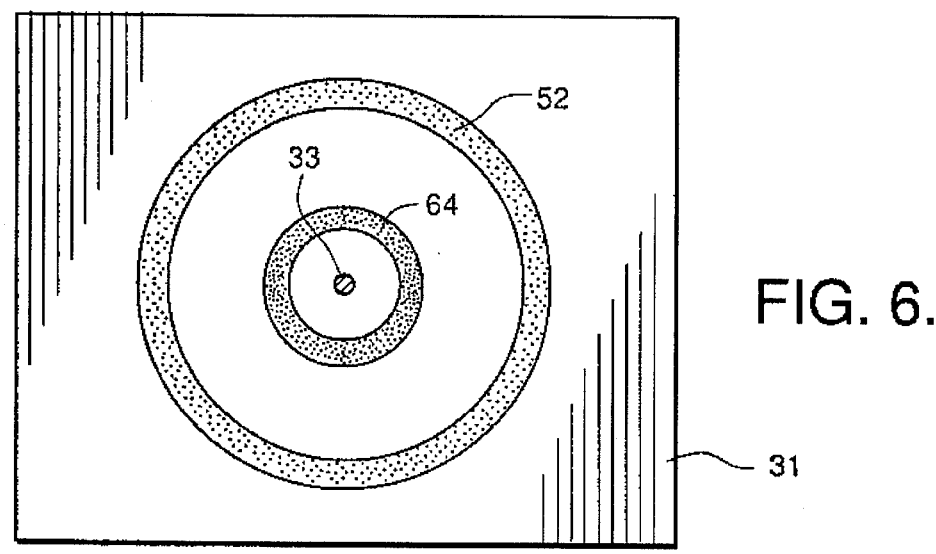
FIG. 6 is a sectional view of a welded workpiece illustrating the power distribution of a circular acoustic array at the weld interface, taken along the section line 6—6 of FIG. 3.

An elevation view taken along line 6—6 of FIG. 3 is shown in FIG. 6, with transmitter light ring 52 and weld 33 shown as if you could see through the workpieces for illustration. As explained above, the transmitter beam light ring 52 has a different diameter than the read-out beam light ring 64. The different ring diameters can contribute to the enhancement of the signal-to-noise, including suppression of spurious off-axis path noise sources, as will be discussed below.

Referring back to FIG. 3, every point on the transmitter light ring 52 acts as a point source of acoustic waves 40 through either thermoelastic or ablation effects. Therefore, the transmitter light ring 52 actually generates an array of acoustic waves that arrive in phase at points in the workpieces 27 and 31 that are centered with respect to the transmitter light ring 52. At these points, the acoustic waves 40 coherently "add", resulting in an acoustic "beam "having a finite diameter that is smaller than would be produced by a typical (1 mm to 2 mm) single laser illumination spot. Post processing filtering is generally required to remove the lower acoustic frequency components, thereby appreciably narrowing the acoustic beam diameter. The diameter of the acoustic beam at any given depth is a function of the transmitter light ring 52 diameter, the wavelength of the acoustic beam and the distance from the transmitter light ring 52, and can in many cases be approximated by the expression:

$$(\lambda/D)*\text{(depth into the sample)}$$

where $\lambda$ is the center wavelength of the acoustic band, and D is the diameter of the light ring. This formula is valid in the limit where the depth into the workpiece under inspection approximates or exceeds D/2, which is typically the case.

Therefore, the diameter of the transmitter light ring 52 can be adjusted so that the coherent addition of the acoustic waves 40 at the weld 33 result in a narrow acoustic beam at the weld 33. Furthermore, when generating shear waves, the transmitter light ring 52 should have a diameter which produces a maximum shear wave (i.e., focused) acoustic pattern at the desired internal probe volume within the workpiece (the weld 33 in FIG. 3). Ideally, in many weld applications, the acoustic waves 40 should combine so that the acoustic beam they form is as wide as the maximum weld 33 diameter at the weld site. This large acoustic beam size applies to the case depicted in FIG. 3, where the fusion size of the weld 33 can be ascertained in a single shot (or, more precisely, with the receiver light ring at a fixed location on the workpiece 31 via acoustic-wave energy transmission through the weld 33. In the case where one desires to determine the dimensions a weld by scanning across the welded region, then a smaller diameter acoustic beam (relative to the weld width) would be preferable, so that a detailed mapping of the weld 33 can be obtained. Either of these conditions can be achieved by choosing appropriate focal lengths for the lens 48 and axicon 50 for a given weld depth (the distance between the surface 25 of the second workpiece 27 and the weld 33). For example, if a weld with a maximum diameter of 1 mm is located 3 mm from the surface 25 of the second workpiece 27, then the transmitter light ring 52 diameter should be approximately 8.5 mm and the focal lengths of the lens 48 and axicon 50 should be chosen appropriately.

Figure 7A:
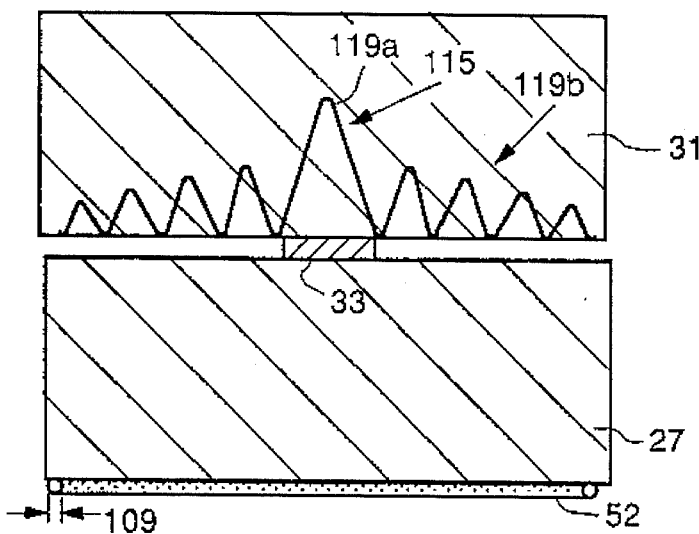
FIG. 7a is an enlarged sectional view of the welded workpieces of FIG. 3 illustrating the acoustic amplitude distribution of a circular acoustic array at the weld interface.

FIG. 7a is an enlarged sectional view of the workpieces illustrating this example. The transmitter light ring 52 is approximately 8.5 mm in diameter and generates acoustic waves (not shown) that coherently add at the weld 33. A cross-section of the acoustic amplitude distribution 115 of the coherently combined acoustic waves is shown. The acoustic beam diameter is defined as the full-width-half-maximum of the central lobe 119a. In this example, the 8.5 mm transmitter light ring 52 diameter results in an acoustic beam diameter at the weld 33 that is approximately equal to the weld 33 diameter (1 mm).

Ideally, the light ring thickness 109 should be infinitesimally small so that all acoustic waves originating from the light ring 52 coherently add at the weld 33. As the light ring thickness 109 is increased, some of the acoustic waves that originate at the light ring 52 do not arrive in phase at the weld 33. Therefore, they interfere destructively at the weld 33 and the amplitude of the central lobe 119a decreases. Therefore, in the preferred embodiment, the light ring thickness 109 should be less than 20 percent of the acoustic wavelength at the highest acoustic frequency.

Referring back to FIG. 3, the transmitted acoustic waves 37 impinge on the upper surface 35 of the second workpiece 31 and a portion of these waves impinge on the read-out ring 64 area. Just as acoustic waves generated by the transmitter light ring 52 arrive in phase at the weld 33, all acoustic waves 37 that are transmitted through the weld 33 and arrive at the read-out ring 64 arrive in-phase over a locus underneath the read-out ring 64 because the weld 33 is centered with respect to the read-out ring 64 This causes the surface underneath the read-out ring 64 to vibrate in-phase. Acoustic waves that are reflected from off-center interface sites arrive substantially out-of-phase with respect to each other and substantially cancel when averaged over the read-out ring 64 area. The canceling out of parasitic reflections dramatically improves the signal-to-noise ratio.

The same light ring thickness criteria that applies to the transmitter light ring 64 applies to the read-out light ring 52. As the read-out light ring thickness is increased, a larger portion of the transmitted acoustic waves 37 destructively interfere at the read-out ring 64, resulting in a smaller signal.

The read-out light ring 64 reflects from the vibrating surface 35 and is phase-modulated in accordance with the amplitudes at the frequencies of the vibrations. As mentioned above, the acoustic waves 40 produced by the transmitter ring 52 arrive in-phase at the weld 33 and thus also arrive in-phase over a locus underneath the read-out ring 64 after transmission through the weld 33.

The reflected, modulated read-out beam 70 is collected by the axicon 68 and lens 66 and is directed back through the quarter-wave plate 65, which converts its circular polarization to a horizontal linear polarization and is reflected by polarizing beam splitter 63. The modulated read-out beam 70 and the reference beam 58 are then directed to the wavefront compensated interferometer 72.

Referring back to FIG. 7a, another potential source of noise is the existence of side-lobes 119b in the acoustic beam. Ideally, as discussed above, the transmitter light ring diameter is chosen so that the acoustic waves "add" to give a narrow central lobe 119a at the weld 33. In practice, the amplitude profile of the acoustic beam at the weld 33 contains side-lobes 119b that are not completely suppressed by changing the diameter of the transmitter light ring 52. These side-lobes 119b are a potential source of noise because they extend beyond the boundaries of the weld site.

Figure 7B:
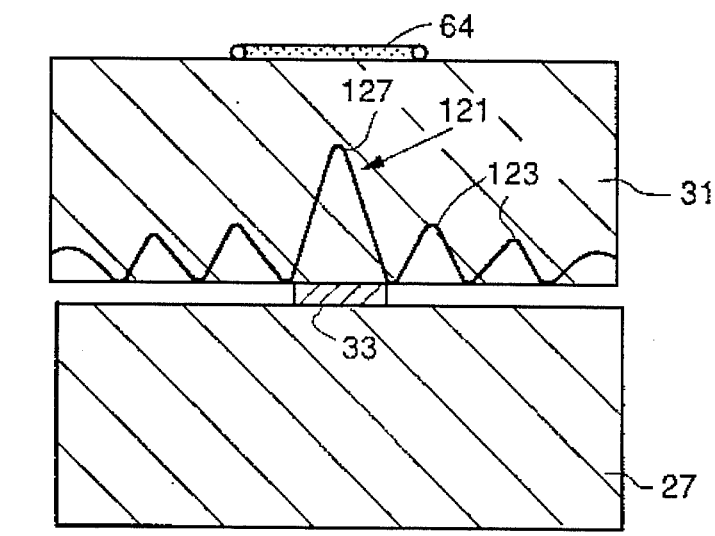
FIG. 7b is an enlarged sectional view of the welded workpieces of FIG. 3 illustrating the sensitivity curve of the read-out light ring for acoustic waves that originate at the weld interface.
Figure 7C:
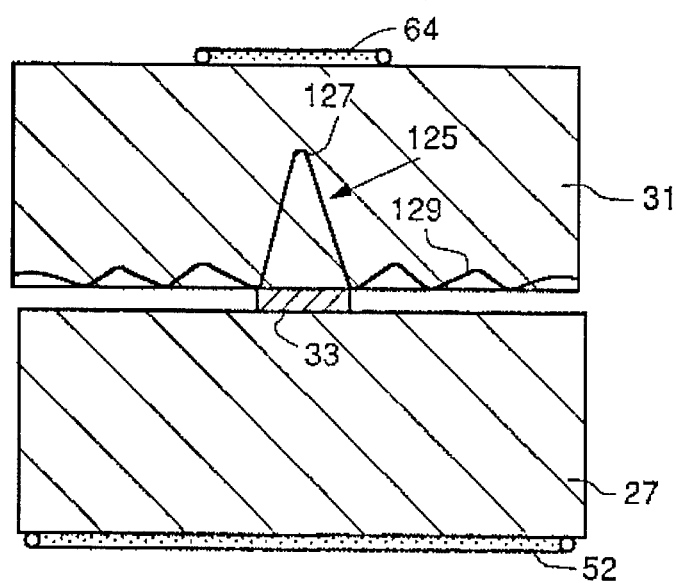
FIG. 7c is a enlarged sectional view of the welded workpieces of FIG. 3 illustrating the composite transmitter-to-read-out light ring coupling curve for a transmitter light ring diameter that is twice that of the read-out light ring diameter.

One way to help mitigate this potential source acoustic-clutter noise is illustrated in FIGS. 7b and 7c. FIG. 7b is a sectional view of the welded workpieces with a cross section of the read-out light ring sensitivity 64 as a function of position along the interface. The read-out light ring sensitivity curve 121 illustrates how well acoustic waves originating from different positions along the interface between workpieces 27 and 31 add up at the read-out light ring 64. In this example, acoustic waves arriving from the weld 33 site arrive substantially in phase and therefore add up to give a strong acoustic signal (central lobe 127). The diameter of the read-out light ring 64 can be adjusted so that the side-lobe structure 123 is substantially out of phase with the side-lobe structure 119b of the transmitter light ring 52 of FIG. 7a.

Since the transmitter-to-receiver coupling is defined by the product of the transmitter power distribution at the weld and the read-out light ring sensitivity curve, the signal contributions from the side-lobes are suppressed. This is illustrated in FIG. 7c. The side-lobe suppression is accomplished by making the read-out light ring 64 diameter less than the transmitter light ring 52 diameter. The resulting transmitter-to-read-out light ring composite coupling curve 125 has the desired narrow central lobe 127 with significant suppression of the side lobes 129.

In order to obtain good spatial resolution with annular sources and receivers, it is required that the sound wave frequency content be restricted to high frequencies, preferably starting at about 5 MHz. A three-to-one, or four-to-one frequency range is typically employed (for example 5 to 15 MHz or 5 to 20 MHz). This provides a good compromise between temporal and spatial resolution.

For some applications, there are additional advantages to high frequency sound wave sources. These include the ability to better suppress undesired surface wave coupling (with single-sided operation), and the ability to increase the system's sensitivity to small flaws or grain size variation in metals.

There are a number of ways of achieving waveforms which emphasize the desired high frequency content, and achieve good temporal resolution. One approach is to use a short pulse burst from a short pulse transmitter beam laser. Three pulses are a good compromise for many applications. This generates a frequency band centered at a frequency which is the inverse of the pulse spacing. However, this leaves an undesired band centered on zero frequency as well. Furthermore, this approach is optically challenging to implement because of the high power levels required.

A preferred approach is to use a single short pulse laser excitation which contains strong high frequency spectral components, and extract the desired bands by filtering the appropriate bands from the pulse out of the receiver. A preferred way of filtering is to split the output pulse and multiply each component by 0.5, invert them, and add them to the original pulse with equal advance and delay relative to it.

Figure 8:
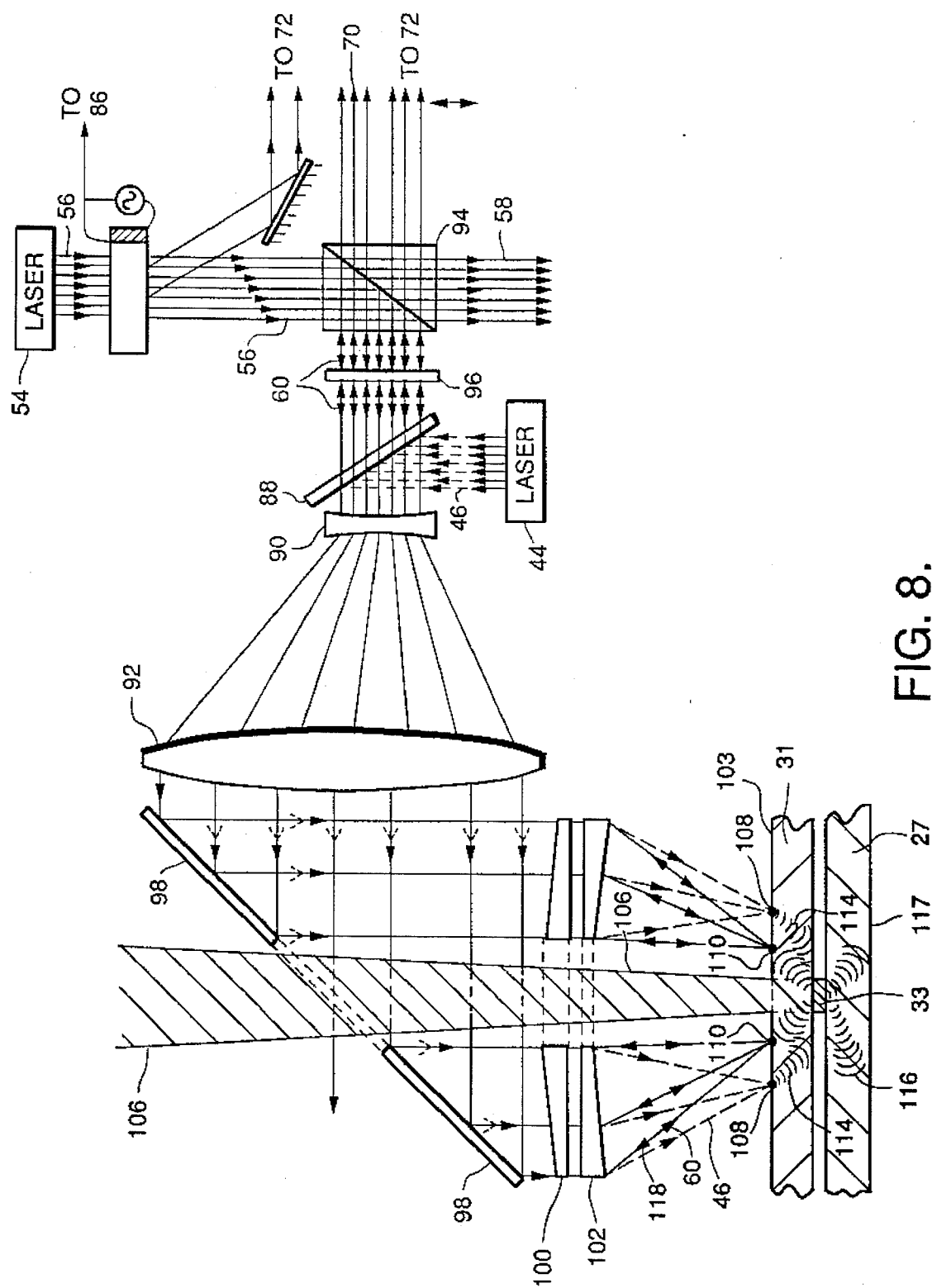
FIG. 8 is a block diagram of a laser-ultrasonic weld inspection system for on-line operation.

A preferred embodiment for on-line use, to interrogate features within a volume, is illustrated in FIG. 8. A pulsed transmitter laser 44, preferably a YAG laser operating at a wavelength 1.06 microns, or a $CO_2$ laser operating at a wavelength of 10.6 microns, is used to generate optical pulses 46 that are typically between 2 and 20 ns in duration. The pulsed beam 46 is directed by a dichroic beam splitter 88 (that only reflects light at the transmitter laser 44 wavelength) to lenses 90 and 92 which expands and collimates the beam 46.

A read-out laser 54, preferably a diode-pumped, continuous-wave (or long-pulsed), doubled-YAG laser operating at a wavelength of 532 nm, is used to generate an optical beam 56 having both horizontal and vertical linear polarization components. A polarizing beam splitter 94 splits the optical beam 56 into a read-out beam 60 and a reference beam 58 by reflecting the vertical polarization component and transmitting the horizontal polarization component.

A quarter-wave plate 96 changes the polarization of the read-out beam 60 from vertical to circular. The read-out beam 60 then passes through the dichroic beam splitter 88 and is expanded and collimated by lenses 90 and 92.

The co-propagating read-out beam 60 and pulsed transmitter beam 46 are then reflected by an annular mirror 98. The transmitter beam 46 and read-out beam 60 are then focused by an annular lens 100 and axicon 102 onto the surface 103 of a first workpiece 31 that is being welded to a second workpiece 27. Both the transmitter beam 46 and the read-out beam 60 are formed into light patterns, preferably ring-shaped patterns 108 and 110 respectively, on the surface of the first workpiece 31 by the annular lens 100 and axicon 102. The centers of the transmitter light ring 108 and the read-out light ring 110 are aligned with the center of the weld 33 to be probed, or are scanned across it if the workpieces are being inspected while they move along an inspection line. Since the transmitter beam 46 and read-out beam 60 have different wavelengths, the bulk and/or grating dispersive property of the annular axicon 102 causes the ring-shaped light patterns 108 and 110 to be of different diameters for optimum side-lobe and clutter-noise suppression.

The annular mirror 98, lens 100, and axicon 102 allow a weld beam, such as a laser or electron-beam welder beam 106, simultaneous access to the workpieces 31 and 27, resulting in the ability to acoustically probe the weld 33 while it is being formed (on-line). The phased-array receiver can also be used in applications where acoustic emission from the weld-joint generates an acoustic beam, whose signature is to be sensed (which would eliminate the need for the transmitter beam 46 that would otherwise be required to induce acoustic waves in the workpiece). In a manner similar to the above system, the acoustic emission can be sensed with a locus of appropriately placed laser probe beams, thereby maximizing the desired signal, while reducing background clutter noise and other spurious acoustic signals.

Figure 9A:
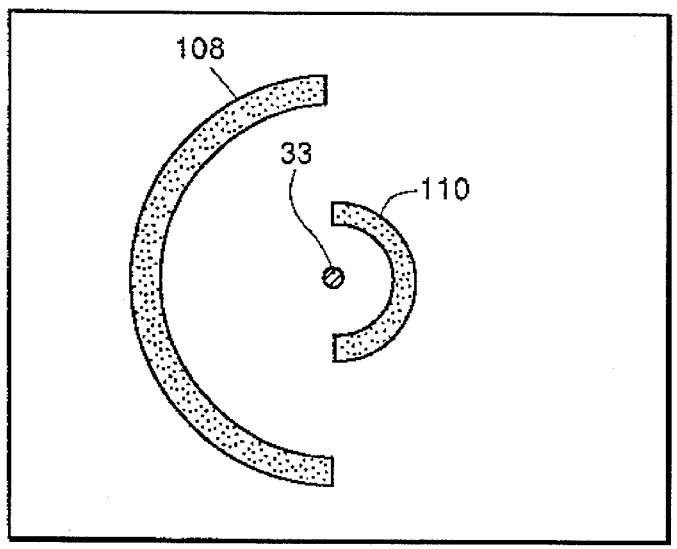
FIGS. 9a and 9b are elevation views taken along the section line 6—6 of FIG. 3, illustrating different light ring geometries that may be utilized.
Figure 9B:
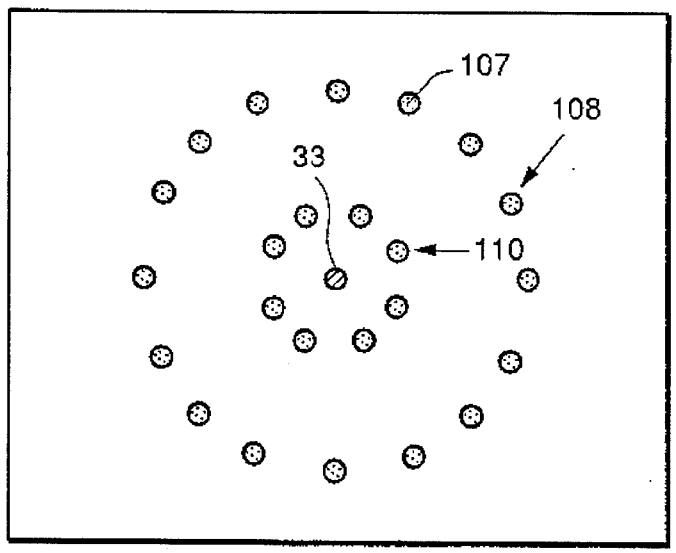
Figure 7A:
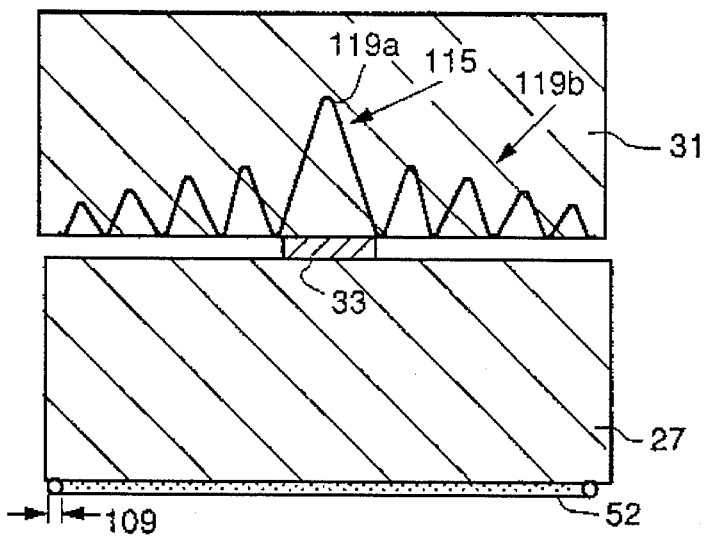
Figure 7B:
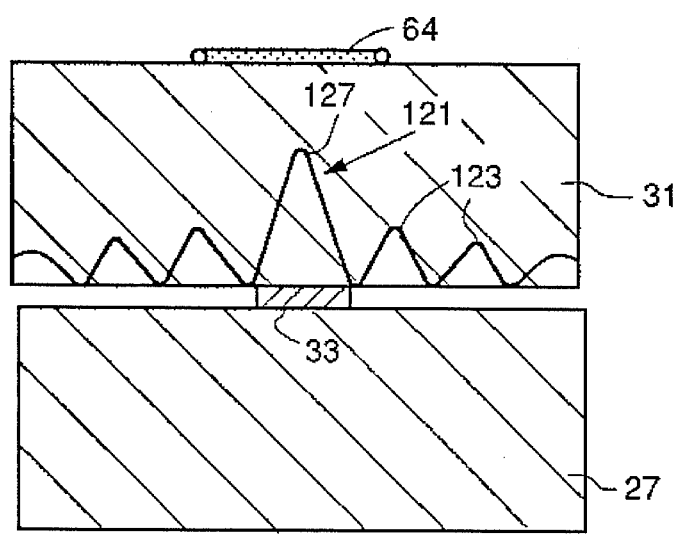
Figure 7C:
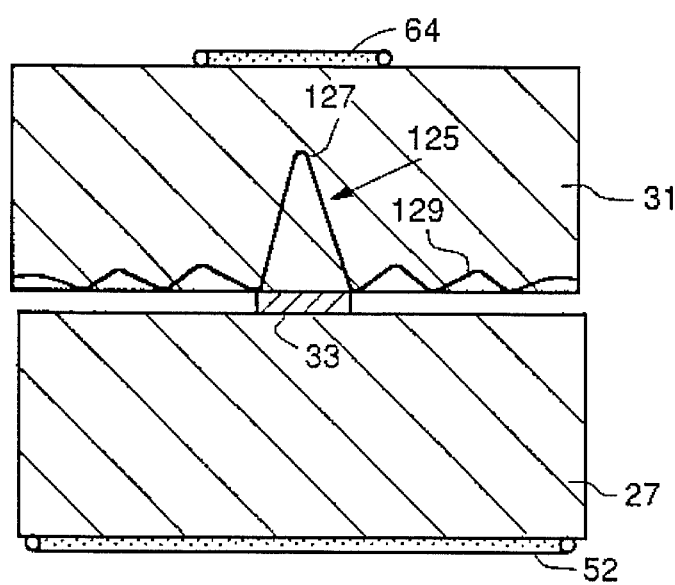

In the embodiment of FIG. 8, the read-out light ring diameter is made half that of the transmitter light ring diameter by choosing a read-out beam 60 with a wavelength that is twice as long as the transmitter beam 46 wavelength and using common dispersive optical elements to form the readout and transmitter light rings on the surface 103 of the first workpiece 31. It is preferable to use transmitter and read-out light patterns that are not fully circular, as illustrated in FIGS. 9a and 9b. The different ring diameters help reduce cross-coupling from ring-to-ring, which could be caused by surface coupling. For example, half rings could be used for the transmitter light pattern 108 and/or the read-out light pattern 110, as illustrated in FIG. 9a. Although the acoustic beam generated by a half-ring is asymmetric (narrow in one dimension and wide in another dimension), with a loss in spatial resolution along the wide part of the beam, there is a significant advantage to this configuration. With single-sided operation, there are additional coupling mechanisms from transmitter to receiver which can restrict the ring geometry. Specifically, the transmitter light ring 108 also generates surface or Raleigh waves which skim the surface 103 of the workpiece 31 and arrive (in phase) at the read-out light ring 110. Although the surface wave path length is shorter than the path length for the double-pass compression waves 114 (which probe the weld), their velocity is almost half of the compression wave 114 velocity. Thus, the surface waves can easily arrive in temporal coincidence with the first arriving compression wave 114 and obscure or otherwise interfere with it. With a rough workpiece surface 103 the surface wave may be sufficiently attenuated, over long propagation paths, that surface wave interference becomes negligible. A semi-circular geometry maximizes the surface wave path length, as discussed below, and thereby also maximizes the surface wave attenuation.

If this is not the case, several alternative solutions are available with short pulse operation. The simplest is to move the transmitter and read-out rings 108 and 110 closer or further apart to eliminate temporal coincidence. A more widely applicable solution is to use semi-circular, oppositely configured, annular rings rather than full circles for the transmitter and read-out rings. This does not fully eliminate the surface wave coupling, but does appreciably reduce it. One reason for the reduction in surface wave coupling is that the effective propagation distance from a source site to the various read-out points on the read-out ring 110 is greatly increased, thereby better attenuating the surface waves through spreading and loss mechanisms.

There is another important effect that effectively eliminates short path coupling with high frequency sound waves. A point source on the transmitter ring 108 induces a surface wave which propagates to the read-out ring 110 with unequal time delays and causes a corresponding surface displacement. At any particular temporal frequency, these displacements are sinusoidal and will induce a large phase shift over the read-out semicircle 110. This phase shift will be several multiples of 360 degrees, and the surface wave induced surface displacements will be effectively integrated over the read-out ring 110. Thus, the average surface displacement induced by the surface wave will sum to substantially zero at the high frequency end, and to low values at the low frequency end of the pulse spectrum. The only exception results from a spherical wave formed by the transmitter ring 108 semi-circle. Such a wave effectively focuses at the ring center, expands, and arrives at the read-out semi-circle ring 110 in phase. However, the propagation distance is maximum for this type of coupling, specifically the sum of the ring radii. Since the surface wave sound velocity is about half that of the compression waves 40, it arrives appreciably later in time than the compression waves 40 that probe the underlying volume (for typical geometries). This differs from full ring systems wherein the surface wave travel distance is the difference in the ring radii. Usually, this geometry results in an overlap of the surface wave and compression wave pulses. However, in rare cases the semicircular geometry yields a pulse overlap and the full ring designs can provide a solution to the problem. For such cases, the surface wave pulse arrives ahead of the compression wave. The Rayleigh arrival pulse amplitude can provide a useful calibration check on the transmitter laser 46 intensity, if the attenuation constant for this wave is known. For all these reasons, half-circle transmitter and read-out light rings are preferred, for single-sided operation.

In addition, the light patterns do not need to be continuous rings. As shown in FIG. 9b, it is possible to use an array of discrete light spots 107 for the transmitter light pattern 108 and/or the read-out light pattern 110, as long as the light spots 107 are arranged symmetrically about the weld 33. However, the strength of the acoustic beam that is generated by the transmitter light pattern 108 and the sensitivity of the read-out light pattern 110 may be reduced as the number of light spots 107 decreases because this reduces the number of acoustic sources. Therefore, continuous light rings are preferred, especially if the laser power must be held below the surface damage threshold of the workpiece.

While several illustrative embodiments of the invention have been shown and described, numerous variations and alternate embodiments will occur to those skilled in the art. For example, a "ring-shape" is not the only transmitter and read-out beam geometries that could be used. Other geometries that will generate an acoustic array and allow the read-out beam to detect only the acoustic waves that probe the weld could be used. Such variations and alternate embodiments are contemplated, and can be made without departing from the spirit and scope of the appended claims.

We claim:

1. A laser-ultrasonic, non-contacting inspection system, comprising:

an acoustic wave generator for generating an array of acoustic waves in a workpiece that arrive substantially in phase with respect to each other at a desired inspection area in said workpiece and propagate through and/or reflect from said inspection area arrive at an area on an outer surface of said workpiece, with said waves arriving substantially in phase with respect to each other over a locus at said outer surface, thereby vibrating said outer surface over said locus, an acoustic wave receiver that detects said acoustic waves over said locus, said acoustic wave receiver comprising an optical beam generator that directs an optical read-out beam to said vibrating surface and distributes it over said locus so that the read-out beam is phase modulated by the vibrations along said locus and reflected from said surface, and a signal monitor for extracting information about said inspection area from said acoustic wave receiver.

2. The system of claim 1, wherein said workpiece comprises first and second workpieces, said inspection area is located between said first and second workpieces, and said acoustic wave generator comprises an optical beam generator for generating an optical beam having a power density sufficient to generate an array of acoustic waves in said first workpiece through either thermoelastic or ablation effects.

3. The system of claim 1, wherein said acoustic wave generator comprises an optical beam generator for directing an optical beam that has a power density sufficient to generate an array of acoustic waves in said workpiece through either thermoelastic or ablation effects onto said workpiece so that said beam is symmetric about said inspection area.

4. The system of claims 3, wherein said symmetric beam falls within a ring-shaped pattern on said first workpiece.

5. The system of claim 4, wherein said beam illuminates a half to full ring-shaped pattern on said first workpiece.

6. The system of claim 3, wherein said optical beam generator distributes said read-out beam over said locus so that it is symmetric about said inspection area.

7. The system claim 6, wherein said symmetric read-out beam falls within a ring-shaped pattern on said vibrating surface.

8. The system of claim 7, wherein said read-out beam illuminates a half to full ring-shaped pattern on said workpiece.

9. A method of inspecting an area in a workpiece, said workpiece also including an outer surface, comprising the steps of:

generating an array of acoustic waves in said workpiece that arrive substantially in phase with respect to each other at said inspection area and propagate through and/or reflect from said inspection area to arrive at an area on an outer surface of said workpiece, with said waves arriving substantially in phase with respect to each other over a locus at said outer surface, thereby vibrating said outer surface over said locus, detecting said acoustic waves over said locus by directing an optical read-out beam to said vibrating surface and distributing it over said locus so that said read-out beam is phase modulated by said vibrations and reflected from said surface, and extracting information about said inspection area from said detected acoustic waves.

10. The method of claim 9, wherein said workpiece comprises first and second workpieces, said inspection area is located between said first and second workpieces, and said array of acoustic waves is generated in said first workpiece by directing an optical beam having a power density sufficient to generate said array of acoustic waves through thermoelastic or ablation effects onto said first workpiece.

11. The method of claim 9, wherein said array of acoustic waves is generated in said workpiece by directing an optical beam that has a power density sufficient to generate an array of acoustic waves in said workpiece through either thermoelastic or ablation effects onto said workpiece so that said beam is symmetric about said inspection area.

12. The method of claim 11, wherein said optical beam is directed to fall within a ring-shaped pattern on said first workpiece.

13. The method of claim 12, wherein said optical beam illuminates a half to full ring-shaped pattern on said workpiece.

14. The method of claim 9, wherein said optical read-out beam is distributed over said locus so that it is symmetric about said inspection area.

15. The method of claim 14, wherein said read-out beam is directed to fall within a ring-shaped pattern on said vibrating surface.

16. The method of claim 15, wherein said read-out beam illuminates a half to full ring-shaped pattern on said vibrating surface.

17. The method of claim 9, further comprising the step of removing phase and amplitude aberrations induced on said optical read-out beam.

18. The method of claim 17, wherein said phase and amplitude aberrations are removed with a double-pumped phase conjugate mirror.

19. The method of claim 17, wherein said phase and amplitude aberrations are removed with a deformable mirror.

20. The method of claim 17, wherein said aberrations are removed with a membrane-based spatial light modulator.

21. The method of claim 9, wherein information about said inspection area is extracted from said acoustic waves by:

generating an optical reference beam having a predetermined phase relationship with said read-out beam, combining said reference beam with said phase modulated read-out beam to generate a beat frequency between said beams, and extracting information about said inspection area from the beat frequency between said reference beam and said modulated read-out beam.

22. A weld inspection system for on-line inspection of a weld site between first and second workpieces, each of said workpieces including an outer surface, comprising:

an acoustic wave generator for generating an array of acoustic waves in said first workpiece that arrive substantially in phase with respect to each other at said weld site such that a portion of said waves reflect from said weld site and propagate back through said first workpiece to arrive at and vibrate an area on the outer surface of said first workpiece, with said waves arriving substantially in phase with respect to each other over a locus at said outer surface, and another portion of said acoustic waves propagate into said second piece through said weld site as a weld joint forms, an acoustic wave receiver that detects said acoustic waves over said locus by directing an optical read-out beam to said vibrating surface and distributing it over said locus so that the read-out beam is phase modulated by the vibrations along said locus and reflected from said surface, and a signal monitor for extracting information about said weld site from said acoustic wave receivers.

23. The system of claim 22, wherein said acoustic wave generator comprises:

a pulsed laser for generating a pulsed transmitter beam with a power density sufficient to generate an array of acoustic waves in said first workpiece through thermoelastic or ablation effects, and a transmitter beam director for directing said transmitter beam to said outer surface of said first workpiece.

24. The system of claim 23, wherein said transmitter beam director comprises:

a transmitter beam expander for expanding the diameter of said transmitter beam, a transmitter beam reflector for directing said transmitter beam to said first workpiece, and a transmitter beam focuser for focusing said transmitter beam onto said first workpiece.

25. The system of claim 24, wherein said transmitter beam reflector comprises an annular mirror for reflecting said transmitter beam while simultaneously allowing a weld beam to access said first and second workpieces.

26. The system of claim 25, wherein said transmitter beam focuser comprises:

an annular lens, and a dispersive annular axicon, said annular lens and axicon forming said transmitter beam into a ring-shaped light pattern on said outer surface of said first workpiece, said annular lens and axicon simultaneously allowing said weld beam to access said workpieces while said transmitter and read-out beams are directed to said first workpiece.

27. The system of claim 22, wherein said acoustic wave receiver comprises:

an optical beam generator for generating said optical read-out beam and a reference beam, and a read-out beam director for directing said read-out beam to said vibrating surface of said first workpiece such that said read-out beam is reflected from said vibrating surface and phase modulated by vibrations induced on by said acoustic waves.

28. The system of claim 27, wherein said read-out beam director comprises:

a read-out beam expander for expanding the diameter of said read-out beam, a read-out beam reflector for directing said read-out beam to said first workpiece, and a read-out beam focuser for focusing said read-out beam onto said first workpiece.

29. The system of claim 28, wherein said read-out beam reflector comprises an annular mirror for reflecting said read-out beam while simultaneously allowing a weld beam to access said workpieces.

30. The system of claim 29, wherein said read-out beam focuser comprises:

an annular lens, and a dispersive annular axicon, said annular lens and axicon forming a ring-shaped light pattern at said outer surface over said locus, said annular lens and axicon simultaneously allowing said weld beam to access said workpieces while said transmitter and read-out beams are directed to said first workpiece.

31. The system of claim 30, wherein said transmitter and read-out beams have different wavelengths.

32. The system of claim 31, wherein said transmitter and read-out beam directors are implemented with common elements.

33. The system of claim 27, wherein said signal monitor comprises:

an optical beam generator for generating an optical reference beam having a predetermined phase relationship with said read-out beam, a beam combiner for combining said reference beam and said phase modulated read-out beam to generate a beat frequency between said beams, a detector for detecting the beat frequency between said reference beam and said phase modulated read-out beam, and a processor for extracting information about said weld joint from said beat frequency.

34. The system of claim 27, further comprising a wavefront compensator for removing phase and amplitude aberrations induced in said phase modulated read-out beam, thereby wavefront compensating said modulated read-out beam.

35. The system of claim 34, wherein said signal monitor comprises:

a beam combiner for combining said wavefront compensated modulated read-out beam and said reference beam, a detector for detecting the beat frequency between said reference beam and said wavefront compensated modulated read-out beam, and a processor for extracting information about said weld joint from said beat frequency.

36. The system of claim 34, wherein said wavefront compensator comprises:

a beam divider for dividing said reference beam into a compensator reference beam and a detector reference beam, a membrane-based spatial light modulator having a readout side for receiving said modulated read-out beam, a write side for receiving said compensator reference beam, and micro-mirrors on said readout side for reflecting said modulated read-out beam, said spatial light modulator removing said phase and amplitude aberrations from said modulated read-out beam, thereby wavefront compensating said modulated read-out beam, and a first beam director for directing said reflected, modulated read-out beam to said write side, thereby forming a feedback loop, said reflected, modulated read-out beam optically interfering with said compensator reference beam at said write side to create an optical interference pattern having an intensity profile on said write side that corresponds to said phase and amplitude aberrations imparted on said modulated read-out beam, said interference pattern on said write side causing a corresponding change in the position of said micro-mirrors on said readout side to correct said phase and amplitude aberrations as said modulated read-out beam undergoes reflection from said micro-mirrors.

37. The system of claim 36, wherein said signal monitor comprises:

a beam combiner for combining said wavefront compensated modulated read-out beam and said detector reference beam, a detector for detecting the beat frequency between said detector reference beam and said wavefront compensated modulated read-out beam, and a processor for extracting information about said weld joint from said beat frequency.

38. The system of claim 35, wherein said wavefront compensator comprises:

a deformable mirror for receiving and reflecting said modulated read-out beam, an array of phase detectors for receiving said reflected, modulated read-out beam, each of said phase detectors in electrical communication with a corresponding area of said deformable mirror, and a first beam director for directing said reflected, modulated read-out beam to said array of detectors for detecting said phase and amplitude aberrations over an incremental portion of said read-out beam and causing a corresponding change in the position of said corresponding area of said deformable mirror to correct said phase and amplitude aberrations as said read-out beam reflects from said deformable mirror.

39. The system of claim 34, wherein said wavefront compensator comprises a double-pumped phase conjugate mirror system.

40. The system of claim 39, wherein said double-pumped phase conjugate mirror system comprises:

a first beam divider for dividing said reference beam into a compensator reference beam and a detector reference beam, and a photorefractive crystal for receiving said modulated read-out beam and said compensator reference beam, said modulated read-out beam and said compensator reference beam writing photorefractive diffraction gratings in said crystal that diffract said modulated read-out beam and removes said phase and amplitude aberrations from said modulated read-out beam, thereby wavefront compensating said modulated read-out beam.

41. The system of claim 40, wherein said signal monitor comprises:

a beam combiner for combining said wavefront compensated modulated read-out beam and said detector reference beam, a detector for detecting the beat frequency between said detector reference beam and said wavefront compensated modulated read-out beam, and a processor for extracting information about said weld joint from said beat frequency.

42. The system of claim 40, further comprising a frequency shifter for shifting the frequency of said compensator reference beam to increase the efficiency of said double-pumped phase conjugator.

43. A weld inspection system for off-line inspection of a weld joint between first and second workpieces, each of said workpieces also including an outer surface, comprising:

an acoustic wave generator for generating an array of acoustic waves in said first workpiece that arrive substantially in phase with respect to each other at said weld joint such that a portion of said waves propagate through said weld joint to arrive at and vibrate an area on the outer surface of said second workpiece, with said waves arriving substantially in phase with respect to each other over a locus at said outer surface, an acoustic wave receiver that detects said acoustic waves over said locus by directing an optical read-out beam to said vibrating surface and distributing it over said locus so that the read-out beam is phase modulated by the vibrations along said locus and reflected from said surface, and a signal monitor for extracting information about said weld site from said acoustic wave receivers.

44. The system of claim 43, wherein said acoustic wave generator comprises:

a pulsed laser for generating a pulsed transmitter beam with a power density sufficient to generate an array of acoustic waves in said first workpiece through thermoelastic or ablation effects, and a transmitter beam director for directing said transmitter beam to said outer surface of said first workpiece.

45. The system of claim 44, wherein said transmitter beam director comprises:

a transmitter beam expander for expanding the diameter of said transmitter beam, a transmitter beam reflector for directing said transmitter beam to said first workpiece, and a transmitter beam focuser for focusing said transmitter beam on to said first workpiece.

46. The system of claim 45, wherein said transmitter beam focuser comprises:

a lens, and a dispersive axicon, said lens and axicon forming said transmitter beam into a ring-shaped light pattern on said outer surface of said first workpiece.

47. The system of claim 43, wherein said acoustic wave receiver comprises:

an optical beam generator for generating said optical read-out beam and a reference beam, and a read-out beam director for directing said read-out beam to said vibrating surface of said second workpiece such that said read-out beam is reflected from said vibrating surface and phase modulated by vibrations induced by said acoustic waves.

48. The system of claim 47, wherein said read-out beam director comprises:

a read-out beam expander for expanding the diameter of said read-out beam, a read-out beam reflector for directing said read-out beam to said first workpiece, and a read-out beam focuser for focusing said read-out beam onto said first workpiece.

49. The system of claim 48, wherein said read-out beam focuser comprises:

a lens, and a dispersive axicon, said lens and axicon forming a ring-shaped light pattern at said outer surface over said locus.

50. The system of claim 47, wherein said signal monitor comprises:

a beam combiner for combining said reference beam and said phase modulated read-out beam, a detector for detecting the beat frequency between said reference beam and said phase modulated read-out beam, and a processor for extracting information about said weld joint from said beat frequency.

51. The system of claim 47, further comprising a wavefront compensator for removing phase and amplitude aberrations induced in said phase modulated read-out beam, thereby wavefront compensating said modulated read-out beam.

52. The system of claim 51, wherein said signal monitor comprises:

an optical beam generator for generating an optical reference beam having a predetermined phase relationship with said read-out beam, a beam combiner for combining said reference beam and said phase modulated read-out beam to generate a beat frequency between said beams, a detector for detecting the beat frequency between said reference beam and said phase modulated readout beam, and a processor for extracting information about said weld joint from said beat frequency.

53. The system of claim 51, wherein said wavefront compensator comprises:

a beam divider for dividing said reference beam into a compensator reference beam and a detector reference beam, a membrane-based spatial light modulator having a readout side for receiving said modulated read-out beam, a write side for receiving said compensator reference beam, and micro-mirrors on said readout side for reflecting said modulated read-out beam, said spatial light modulator removing said phase and amplitude aberrations from said modulated read-out beam, thereby wavefront compensating said modulated read-out beam, and a first beam director for directing said reflected, modulated read-out beam to said write side, thereby forming a feedback loop, said reflected, modulated read-out beam optically interfering with said compensator reference beam at said write side to create an optical interference pattern having an intensity profile on said write side that corresponds to said phase and amplitude aberrations imparted on said modulated read-out beam, said interference pattern on said write side causing a corresponding change in the position of said micromirrors on said readout side to correct said phase and amplitude aberrations as said modulated read-out beam undergoes reflection from said micro-mirrors.

54. The system of claim 53, wherein said signal monitor comprises:

a beam combiner for combining said wavefront compensated modulated read-out beam and said detector reference beam, a detector for detecting the beat frequency between said detector reference beam and said wavefront compensated modulated read-out beam, and a processor for extracting information about said weld joint from said beat frequency.

55. The system of claim 52, wherein said wavefront compensator comprises:

a deformable mirror for receiving and reflecting said modulated read-out beam, an array of phase detectors for receiving said reflected, modulated read-out beam, each of said phase detectors in electrical communication with a corresponding area of said deformable mirror, and a first beam director for directing said reflected, modulated read-out beam to said array of detectors for detecting said phase and amplitude aberrations over an incremental portion of said read-out beam and causing a corresponding change in the position of said corresponding area of said deformable mirror to correct said phase and amplitude aberrations as said read-out beam reflects from said deformable mirror.

56. The system of claim 51, wherein said wavefront compensator comprises a double-pumped phase conjugate mirror system.

57. The system of claim 56, wherein said double-pumped phase conjugate mirror system comprises:

a first beam divider for dividing said reference beam into a compensator reference beam and a detector reference beam, and a photorefractive crystal for receiving said modulated read-out beam and said compensator reference beam, said modulated read-out beam and said compensator reference beam writing photorefractive diffraction gratings in said crystal that diffract said modulated read-out beam and removes said phase and amplitude aberrations from said modulated read-out beam, thereby wavefront compensating said modulated read-out beam.

58. The system of claim 57, wherein said signal monitor comprises:

a beam combiner for combining said wavefront compensated modulated read-out beam and said detector reference beam, a detector for detecting the beat frequency between said detector reference beam and said wavefront compensated modulated read-out beam, and a processor for extracting information about said weld joint from said beat frequency.

59. A laser-ultrasonic, non-contacting inspection system, comprising:

an acoustic wave generator for generating an array of acoustic waves in a workpiece that arrive substantially in phase with respect to each other at a desired inspection area in said workpiece and propagate through and/or reflect from said inspection area to illuminate an area on an outer surface of said workpiece, with said waves arriving substantially in phase with respect to each other over a locus at said outer surface, thereby vibrating the illuminated surface, said generator comprising an optical beam generator that directs an optical beam that has a power density sufficient to generate an array of acoustic waves in said workpiece through either thermoelastic or ablation effects onto said workpiece so that said beam is symmetric about said inspection area, an acoustic wave receiver that detects said acoustic waves over said locus, said acoustic wave receiver comprising an optical beam generator that directs a read-out beam onto said vibrating surface so that said read-out beam falls within a ring-shaped pattern on said vibrating surface that is symmetric about said inspection area, said read-out beam being phase modulated by said vibrations and reflected from said surface, and a signal monitor for extracting information about said inspection area from said acoustic wave receiver.

60. The system of claim 59, wherein said read-out beam illuminates a half to full ring-shaped pattern on said workpiece.

61. A method of inspecting an area in a workpiece, said workpiece also including an outer surface, comprising the steps of:

generating an array of acoustic waves in said workpiece that arrive substantially in phase with respect to each other at said inspection area and propagate through and/or reflect from said inspection area to illuminate an area on an outer surface of said workpiece, with said waves arriving substantially in phase with respect to each other over a locus at said outer surface, thereby vibrating the illuminated surface, said acoustic waves being generated in said workpiece by directing an optical beam that has a power density sufficient to generate an array of acoustic waves in said workpiece through either thermoelastic or ablation effects onto said first workpiece so that said beam is symmetric about said inspection area, detecting said acoustic waves over said locus by directing a read-out beam onto said vibrating surface so that said read-out beam falls within a ring-shaped pattern on said vibrating surface that is symmetric about said inspection area, is phase modulated by said vibrations and is reflected from said surface, said read-out beam illuminating a half to full ring-shaped pattern on said vibrating surface, and extracting information about said inspection area from said detected acoustic waves.

62. A method of inspecting an area in a workpiece, said workpiece also including an outer surface, comprising the steps of:

generating an array of acoustic waves in said workpiece that arrive substantially in phase with respect to each other at said inspection area and propagate through and/or reflect from said inspection area to arrive at an area on an outer surface of said workpiece, with said waves arriving substantially in phase with respect to each other over a locus at said outer surface, thereby vibrating said outer surface over said locus, detecting said acoustic waves over said locus by directing an optical read-out beam onto said vibrating surface at said locus so that the read-out beam is phase modulated by said vibrations and reflected from said surface, removing phase and amplitude aberrations induced on said optical read-out beam, extracting information about said inspection area from said detected acoustic waves.

63. A weld inspection system for on-line inspection of a weld site between first and second workpieces, each of said workpieces including an outer surface, comprising:

a pulsed laser that generates a pulsed transmitter beam, a transmitter beam expander that expands the diameter of said transmitter beam, a transmitter beam reflector that directs said transmitter beam to the outer surface of said first workpiece, said reflector comprising an annular mirror that reflects said transmitter beam while simultaneously allowing a weld beam to access said first and second workpieces, a transmitter beam focuser that focuses said transmitter beam onto the outer surface of said first workpiece, said transmitter beam having a power density sufficient to generate an array of acoustic waves in said first workpiece through thermoelastic or ablation effects, said acoustic waves arriving substantially in phase with respect to each other at said weld site such that a portion of said waves reflect from said weld site and propagate back through said first workpiece to illuminate and vibrate an area on the outer surface of said first workpiece, with said waves arriving substantially in phase with respect to each other over a locus at said outer surface, and another portion of said acoustic waves propagate into said second piece through said weld site as a weld joint forms, an acoustic wave receiver that detects said acoustic waves over said locus, and a signal monitor for extracting information about said weld site from said acoustic wave receivers.

64. The system of claim 63, wherein said transmitter beam focuser comprises:

an annular lens, and a dispersive annular axicon, said annular lens and axicon forming said transmitter beam into a ring-shaped light pattern on said outer surface of said first workpiece, said annular lens and axicon simultaneously allowing said weld beam to access said workpieces while said transmitter and read-out beams are directed to said first workpiece.

65. A weld inspection system for on-line inspection of a weld site between first and second workpieces, each of said workpieces including an outer surface, comprising:

an acoustic wave generator for generating an array of acoustic waves in said first workpiece that arrive substantially in phase with respect to each other at said weld site such that a portion of said waves reflect from said weld site and propagate back through said first workpiece to illuminate and vibrate an area on the outer surface of said first workpiece, with said waves arriving substantially in phase with respect to each other over a locus at said outer surface, and another portion of said acoustic waves propagate into said second piece through said weld site as a weld joint forms, an optical beam generator that generates an optical read-out beam and reference beam, a read-out beam expander that expands the diameter of said read-out beam, a read-out beam reflector that directs said read-out beam to said first workpiece such that said read-out beam is reflected from said vibrating surface and phase modulated by vibrations induced by said acoustic waves, said read-out beam reflector comprising an annular mirror that reflects said read-out beam while simultaneously allowing a weld beam to access said workpieces, a read-out beam focuser that focuses said read-out beam onto said first workpiece, and a signal monitor for extracting information about said weld site from said phase modulated read-out beam.

66. The system of claim 65, wherein said read-out beam focuser comprises:

an annular lens, and a dispersive annular axicon, said annular lens and axicon forming a ring-shaped light pattern at said outer surface over said locus, said annular lens and axicon simultaneously allowing said weld beam to access said workpieces while said transmitter and read-out beams are directed to said first workpiece.

67. The system of claim 66, wherein said transmitter and read-out beams have different wavelengths.

68. The system of claim 31, wherein said transmitter and read-out beam directors are implemented with common elements.

69. A weld inspection system for off-line inspection of a weld joint between first and second workpieces, each of said workpieces also including an outer surface, comprising:

an acoustic wave generator for generating an array of acoustic waves in said first workpiece that arrive substantially in phase with respect to each other at said weld joint such that a portion of said waves propagate through said weld joint to illuminate and vibrate an area on the outer surface of said second workpiece, with said waves arriving substantially in phase with respect to each other over a locus at said outer surface, an optical beam generator that generates an optical read-out beam and reference beam, a read-out beam expander that expands the diameter of said read-out beam, a read-out beam reflector that directs said read-out beam to said first workpiece such that said read-out beam is reflected from said vibrating surface and phase modulated by vibrations induced by said acoustic waves, a read-out beam focuser that focuses said read-out beam onto said first workpiece, said focuser comprising a lens and dispersive axicon that together form a ring-shaped light pattern at said vibrating surface over said locus, and a signal monitor for extracting information about said weld site from said acoustic wave receivers.

* * * * *